United States Patent
Hone et al.

(10) Patent No.: US 6,500,419 B1
(45) Date of Patent: Dec. 31, 2002

(54) METHOD FOR INTRODUCING AND EXPRESSING RNA IN ANIMAL CELLS

(75) Inventors: David M. Hone, Ellicott City, MD (US); George Lewis, Baltimore, MD (US); Robert Powell, Baltimore, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 0 days.

(21) Appl. No.: 09/545,153

(22) Filed: Apr. 7, 2000

Related U.S. Application Data

(63) Continuation-in-part of application No. PCT/US98/21093, filed on Oct. 7, 1998.
(60) Provisional application No. 60/061,396, filed on Oct. 7, 1997.

(51) Int. Cl.$^7$ .............................. A61K 48/00; C12N 1/21; C12N 15/87
(52) U.S. Cl. .................. 424/93.2; 424/93.1; 435/252.3; 435/320.1; 435/455; 514/44
(58) Field of Search ........................... 435/320.1, 252.3, 435/455; 424/93.1, 93.2; 514/44

(56) References Cited

U.S. PATENT DOCUMENTS

| | | | |
|---|---|---|---|
| 4,937,190 A | | 6/1990 | Palmenberg et al. ........ 435/69.1 |
| 5,135,855 A | * | 8/1992 | Moss et al. ................. 435/69.1 |
| 5,358,856 A | | 10/1994 | Baltimore et al. .......... 435/69.1 |
| 5,389,368 A | | 2/1995 | Gurtiss, III .............. 424/200.1 |
| 5,877,159 A | | 3/1999 | Powell et al. ................. 514/44 |

FOREIGN PATENT DOCUMENTS

| | | |
|---|---|---|
| EP | 0211543 | 2/1987 |
| WO | WO96/34631 | 11/1996 |
| WO | 97/08955 | 3/1997 |

OTHER PUBLICATIONS

Stuart H. Orkin et al., Report and Recommendations of the panel to assess the NIH investment in research on gene therapy, pp. 1–20.*

S.N. Chatfield et al., Use of the nirB promoter to direct the stable expression of heterologous antigens in salmonella oral vaccine stains: development of a single–dose oral tetanous vaccine, Bio/Technology, vol. 10 8/92, pp. 888–892.*

B.B. Finlay, Molecular and Cellular Mechanisms of Salmonella Pathogenesis, pp. 163–183.*

C. Parsot, *Shigella flexneri*: Genetics of Entry and Intracellular Dissemination in Epithelial Cells, pp. 217–235.*

He et al, *Gene*, 164:75–79 (1995).
Chatfield et al.*Bio/Technology*, 10:888–892 (1992).
Biasolo et al, *J. Virol.*, 70 (4) :2154–2161 (1996).
Duke et al, *J. Virol.*, 66 (3) :1602–1609 (1992).
Falkow, *Annu. Rev. Cell Biol.*, 8:333–363 (1992).
Fouts et al, *Vaccine*, 13 (6) :561–569 (1995).
Goebel et al, "Cytolysins and the Intracellular Life of Bacteria", *Comment* (1997).
Hess et al, *Infect. Immun.*, 63 (5) :2047–2053 (1995).
Hone et al, *Microbial. Pathogen.*, 5:407–418 (1988).
Isberg et al, *Annu Rev. Genet.*, 27:395–422 (1994).
Kärnell et al, *Vaccine*, 13 (1) :88–99 (1995).
Kotloff et al, *Infect. Immun.*, 64 (11) :4542–4548 (1996).
Lu et al, *Cancer Gene Therapy*, 1(4) :267–277 (1994).
Marschall et al, *Cell. Mol. Neurobiology*, 14 (5) :523–536 (1994).
Sizemore et al, *Science*, 270:299–302 (1995).
Wu et al , *Infect. Immun.*, 63 (12) :4933–4938 (1995).

* cited by examiner

*Primary Examiner*—Scott D. Priebe
(74) *Attorney, Agent, or Firm*—Sughrue Mion, PLLC

(57) ABSTRACT

The invention pertains to a method for introducing RNA molecules into eukaryotic cells, wherein the RNA molecules are capable of being translated in the eukaryotic cells or is an antisense RNA or a catalytic RNA, as well as to such bacteria, compositions comprising such bacteria, and nucleic acids which can be introduced into bacteria for practicing the method of the invention. Examples of products the RNA molecule may encode include vaccine antigens, therapeutic agents, immunoregulatory agents or anti-sense RNA molecules or catalytic RNA molecules.

50 Claims, 4 Drawing Sheets

Figure 1

GTTAT TTTCCACCAT ATTGCCGTCT TTTGGCAATG

TGAGGGCCCG GAAACCTGGC CCTGTCTTCT TGACGAGCAT TCCTAGGGGT

CTTTCCCCTC TCGCCAAAGG AATGCAAGGT CTGTTGAATG TCGTGAAGGA

AGCAGTTCCT CTGGAAGCTT CTTGAAGACA AACAACGTCT GTAGCGACCC

TTTGCAGGCA GCGGAACCCC CCACCTGGCG ACAGGTGCCT CTGCGGCCAA

AAGCCACGTG TATAAGATAC ACCTGCAAAG GCGGCACAAC CCCAGTGCCA

CGTTGTGAGT TGGATAGTTG TGGAAAGAGT CAAATGGCTC TCCTCAAGCG

TATTCAACAA GGGGCTGAAG GATGCCCAGA AGGTACCCCA TTGTATGGGA

TCTGATCTGG GGCCTCGGTG CACATGCTTT ACATGTGTTT AGTCGAGGTT

AAAAAACGTC TAGGCCCCCC GAACCACGGG GACGTGGTTT TCCTTTGAAA

AACACGATGA TAAT             (SEQ ID NO: 1)

Auto-amplified RNA for cytoplasmic expression of target gene

Cytoplasmic-launch Env RNA vector:-
Cytoplasmic expression of Env

METHOD FOR INTRODUCING AND EXPRESSING RNA IN ANIMAL CELLS

CROSS-REFERENCE TO RELATED APPLICATIONS

This application is a continuation-in-part of PCT application Number PCT/US98/21093, entitled "*Method for Introducing and Expressing RNA in Animal Cells,*" filed Oct. 7, 1998, which claims the benefit of U.S. Provisional Application No. 60/061,396, filed Oct. 7, 1997. These applications are specifically incorporated by referenced herein.

STATEMENT OF RIGHTS

This invention was made in the course of work supported by the U.S. Government (NIH Grant Nose. 5R21AI42603-02 and 1R21AI42603-01). The U.S. Government has certain rights in the invention.

BACKGROUND OF THE INVENTION

The advent of recombinant DNA technology has greatly accelerated the development of vaccines to control epidemic, endemic, and pandemic infectious diseases (Woodrow et al, *New Generation Vaccines: The Molecular Approach*, Eds., Marcel Dekker, Inc., New York, N.Y. (1989); Cryz, *Vaccines and Immunotherapy*, Ed., Pergamon Press, New York, N.Y. (1991); and Levine et al, *Ped. Ann.*, 22:719–725 (1993)). In particular, this technology has enabled the growth of nucleic acid vaccines. Although the first nucleic acid vaccine was only reported in 1992, the study of nucleic acid vaccines has grown dramatically and examples of this approach have been reported in a wide array of animals using numerous antigens (Tang, D. C., et al. (1992) *Nature* 356:152; Fynan, E. F. et al. (1993) *PNAS USA* 90:11478; Donnelly, J. J. et al. (1995) *Nat Med* 1:583; Wang, B. et al. (1993) *PNAS USA* 90:4156; Davis, H. L., et al. (1993) *Hum Mol Genet* 2:1847; Ulmer, J. B. et al. (1993) *Science* 259:1745; Robinson, H. L. et al. (1993) *Vaccine* 11:957; Eisenbraun, M. D. et al. (1993) *DNA Cell Biol* 12:791; Wang, B. et al. (1994) *AIDS Res Hum Retroviruses* 10:S35; Coney, L. et al. (1994) *Vaccine* 12:1545; Sedegah, M. et al. (1994) *Proc Natl Acad Sci USA* 91:9866; Raz, E. et al. (1994) *Proc Natl Acad Sci USA* 91:9519; Xiang, Z. Q. et al. (1994) *Virology* 199:132) (for a more comprehensive list see www.genweb.com/ Dnavax/Biblio/articles). Early murine experiments with HIV-1 DNA vaccines produced impressive immunological responses, including neutralizing antibody responses against HIV-1 and strong CTL responses against several HIV-1 antigens (Wang, B. et al. (1993) supra; Wang, B. et al. (1994) supra; Coney, L. et al. (1994) supra; Lu, S. et al. (1995) *Virology* 209:147; Shiver, J. W. et al. (1995) *Annals of the New York Academy of Sciences* 772:198; Wahren, B. et al. (1995) *Ann N Y Acad Sci* 772:278). However, an initial attempt to induce protective immunity with an SIV DNA vaccine in Rhesus monkeys was disappointing (Lu, S. et al. (1996) *J Virol* 70:3978). In contrast, an HIV-1$_{MN}$ Env DNA vaccine induced measurable protection against a chimeric SIV/HIV (SHIV) challenge in vaccinated cynomologous macaques (Boyer, J. D. et al. (1996) *Journal of Medical Primatology* 25:242). More recently, intramuscular immunization of chimpanzees with this latter vaccine engendered protection against parenteral challenge with HIV-1$_{SF-2}$ (Boyer, J. D. et al. (1997) *Nature Medicine* 3:526). These differences may have resulted from antigenic differences in the vaccines or differences in the potency of the challenges (Lu, S. et al. (1996) supra; Boyer, J. D. et al. (1996) supra; Boyer, J. D. et al. (1997) supra). It is noteworthy to mention that in the aforementioned chimpanzee study, DNA vaccination only induced modest humoral and cellular responses despite giving 9 doses of vaccine containing a total of 2.9 mg of DNA before challenge (Boyer, J. D. et al. (1997) supra). Thus, although these results are encouraging, the immunogenicity of HIV-1 DNA vaccines must be improved before this approach achieves practical utility in large scale vaccination programs.

The mechanism though which DNA vaccines induce immunity is not fully understood. Muscle cells express low levels of MHC class 1 and do not express detectable levels of co-stimulatory molecules B7-1 and B7-2 (review by Ertl, H. C. and Z. Q. Xiang (1996) *Journal of Immunology* 156:3579). While it remains conceivable that muscle cells may serve as an antigen depot (Ertl and Xiang (1996) supra), their participation in the induction of MHC class I and II responses may be secondary to other antigen presenting cells (Ertl and Xiang (1996) supra). Xiang and Ertl (Ertl and Xiang (1996) supra; Xiang, Z. and H. C. Ertl (1995) *Immunity* 2:129) have suggested that resident dendritic cells may be involved in the primary inductive events. They showed that co-expression of GM-CSF, a cytokine know to activate growth of dendritic cells, at the site of inoculation resulted in a more rapid response to DNA vaccine encoded antigens (Xiang and Ertl (1995) supra). In contrast, co-expression of IFN-γ diminished the responses (Xiang and Ertl (1995) supra). In agreement, Manickan et al. ((1997) *Journal of Leukocyte Biology* 61:125) showed that immunization with dendritic cells transfected with a DNA vaccine induced elevated immune responses, compared to the identical DNA vaccine given alone. In addition, dendritic cells have been shown to express antigen following intradermal vaccination with a DNA vaccines (Raz, E. et al. (1994) supra). Although inconclusive, these data strongly suggest that dendritic cells may play a substantial role in the presentation of DNA vaccine-encode antigens.

Another new class of vaccines are bacterial vector vaccines (Curtiss, In: *New Generation Vaccines: The Molecular Approach*, Ed., Marcel Dekker, Inc., New York, N.Y., pages 161–188 and 269–288 (1989); and Mims et al, In: *Medical Microbiology*, Eds., Mosby-Year Book Europe Ltd., London (1993)). These vaccines can enter the host, either orally, intranasally or parenterally. Once gaining access to the host, the bacterial vector vaccines express an engineered prokaryotic expression cassette contained therein that encodes a foreign antigen(s). Foreign antigens can be any protein (or part of a protein) or combination thereof from a bacterial, viral, or parasitic pathogen that has vaccine properties (*New Generation Vaccines: The Molecular Approach*, supra; *Vaccines and Immunotherapy*, supra; Hilleman, *Dev. Biol. Stand.*, 82:3–20 (1994); Formal et al, *Infect. Immun.* 34:746–751 (1981); Gonzalez et al, *J. Infect. Dis.*, 169:927–931 (1994); Stevenson et al, *FEMS Lett.*, 28:317–320 (1985); Aggarwal et al, *J. Exp. Med.*, 172:1083–1090 (1990); Hone et al, *Microbial. Path.*, 5:407–418 (1988); Flynn et al, *Mol. Microbiol.*, 4:2111–2118 (1990); Walker et al, *Infect. Immun.*, 60:4260–4268 (1992); Cardenas et al, *Vacc.*, 11:126–135 (1993); Curtiss et al, *Dev. Biol. Stand.*, 82:23–33 (1994); Simonet et al, *Infect. Immun.*, 62:863–867 (1994); Charbit et al, *Vacc.*, 11:1221–1228 (1993); Turner et al, *Infect. Immun.*, 61:5374–5380 (1993); Schodel et al, *Infect. Immun.*, 62:1669–1676 (1994); Schodel et al, *J. Immunol.*, 145:4317–4321 (1990); Stabel et al, *Infect. Immun.*, 59:2941–2947 (1991); Brown, *J. Infect. Dis.*, 155:86–92 (1987); Doggett et al, *Infect. Immun.*, 61:1859–1866 (1993);

Brett et al, *Immunol.*, 80:306–312 (1993); Yang et al, *J. Immunol.*, 145:2281–2285 (1990); Gao et al, *Infect. Immun.*, 60:3780–3789 (1992); and Chatfield et al, *Bio/Technology*, 10:888–892 (1992)). Delivery of the foreign antigen to the host tissue using bacterial vector vaccines results in host immune responses against the foreign antigen, which provide protection against the pathogen from which the foreign antigen originates (Mims, *The Pathogenesis of Infectious Disease*, Academic Press, London (1987); and *New Generation Vaccines: The Molecular Approach*, supra).

Of the bacterial vector vaccines, live oral Salmonella vector vaccines have been studied most extensively. There are numerous examples showing that Salmonella vectors are capable of eliciting humoral and cellular immunity against bacterial, viral and parasitic antigens (Formal et al, *Infect. Immun.*, 34:746–751 (1981); Gonzalez et al, supra; Stevenson et al, supra; Aggarwal et al, supra; Hone et al, supra; Flynn et al, supra; Walker et al, supra; Cardenas et al, supra; Curtiss et al, supra; Simonet et al, supra; Charbit et al, supra; Turner et al, supra; Schodel et al, supra, Schodel et al (1990), supra; Stabel et al, supra; Brown, supra; Doggett et al, supra; Brett et al, supra; Yang et al, supra; Gao et al, supra; and Chatfield et al, supra). These humoral responses occur in the mucosal (Stevenson et al, supra; Cardenas et al, supra; Walker et al, supra; and Simonet et al, supra) and systemic compartments (Gonzalez et al, supra; Stevenson et al, supra; Aggarwal et al, supra; Hone et al, supra; Flynn et al, supra; Walker et al, supra; Cardenas et al, supra; Curtiss et al, supra; Simonet et al, supra; Charbit et al, supra; Turner et al, supra; Schodel et al, supra, Schodel et al (1990), supra; Stabel et al, supra; Brown, supra; Doggett et al, supra; Brett et al, supra; Yang et al, supra; Gao et al, supra; and Chatfield et al, supra). Live oral Salmonella vector vaccines also elicit T cell responses against foreign antigens (Wick et al, *Infect. Immun.*, 62:4542–4548 (1994)). These include antigen-specific cytotoxic CD8⁻T cell responses (Gonzalez et al, supra; Aggarwal et al, supra; Flynn et al, supra; Turner et al, supra; and Gao et al, supra).

Ideally, bacterial vector vaccines are genetically defined, attenuated and well-tolerated by the recipient animal or human, and retain immunogenicity (Hone et al, *Vaccine*, 9:810–816 (1991); Tacket et al, *Infect. Immun.*, 60:536–541 (1992); Hone et al, *J. Clin. Invest.*, 90:412–420 (1992); Chatfield et al, *Vaccine*, 10:8–11 (1992); Tacket et al, *Vaccine*, 10:443–446 (1992); and Mims, supra). Recently, the number of potential bacterial vector vaccines for the delivery of prokaryotic expression cassettes has grown. They now include, but are not restricted to *Yersinia enterocolitica* (van Damme et al, *Gastroenterol.*, 103:520–531 (1992)), *Shigella* spp. (Noriega et al, *Infect. Immun.*, 62:5168–5172 (1994)), *Vibrio cholerae* (Levine et al, In: *Vibrio cholerae, Molecular to Global Perspectives*, Wachsmuth et al, Eds, ASM Press, Washington, D.C., pages 395–414 (1994)), Mycobacterium strain BCG (Lagranderie et al, *Vaccine*, 11:1283–1290 (1993); Flynn, *Cell. Molec. Biol.*, 40(Suppl.1):31–36 (1994)), and *Listeria monocytogenes* (Schafer et al, *J. Immunol.*, 149:53–59 (1992)) vector vaccines.

The commercial application of DNA delivery technology to animal cells is broad and includes, in addition to vaccine antigens, delivery of immunotherapeutic agents and therapeutic agents (Darris et al, *Cancer*, 74(3 Suppl.):1021–1025 (1994); Magrath, *Ann. Oncol.*, 5(Suppl 1):67–70 (1994); Milligan et al, *Ann. NY Acad. Sci.*, 716:228–241 (1994); Schreier, *Pharma. Acta Helv.*, 68:145–159 (1994); Cech, *Biochem. Soc. Trans.*, 21:229–234 (1993); Cech, *Gene*, 135:33–36 (1993); Long et al, *FASEB J.*, 7:25–30 (1993); and Rosi et al, *Pharm. Therap.*, 50:245–254 1991)).

The delivery of endogenous and foreign genes to animal tissue for gene therapy has shown significant promise in experimental animals and volunteers (Nabel, *Circulation*, 91:541–548 (1995); Coovert et al, *Curr. Opin. Neuro.*, 7:463–470 (1994); Foa, *Bill. Clin. Haemat.*, 7:421–434 (1994); Bowers et al, *J. Am. Diet. Assoc.*, 95:53–59 (1995); Perales et al, *Eur. J. Biochem.*, 226:255–266 (1994); Danko et al, *Vacc.*, 12:1499–1502 (1994); Conry et al, *Canc. Res.*, 54:1164–1168 (1994); and Smith, *J. Hemat.*, 1:155–166 (1992)).

From the onset nucleic acid vaccine studies focused on the use of DNA vaccines (Tang et al. (1992) supra; Fynan et al. (1993) supra; Donnelly et al. (1995) supra; Wang et al. (1993) supra; Davis et al. (1993) supra; Ulmer et al. (1993) supra; Robinson et al. (1993) supra; Eisenbraun et al. (1993) supra; Wang et al. (1994) supra; Coney et al. (1994) supra; Sedegah et al. (1994) supra; Raz et al. (1994) supra; Xiang et al. (1994) supra). More recently the use of RNA vaccines has been proposed as an alternative approach to the injection of DNA based nucleic vaccines (Zhou, X. et al. (1994) *Vaccine* 12:1510; Conry, R. M. et al. (1995) *Cancer Res* 55:1397). In support, "naked" RNA vaccines have proven modestly immunogenic in mice (Zhou et al. (1994) supra; Conry et al. (1995) supra). An RNA vaccine based on a recombinant Semliki Forrest Virus that expressed the SIV-PBj14 Env gene engendered protection against SIV-PBj14 (Mossman, S. P. et al. (1997) *Journal of Virology* 70:1953).

RNA vaccines would offer two main advantages of over DNA vaccines. First, RNA vaccines would avoid placing vaccinees at risk of an integration event, which over a human life span might lead to the development of malignancy. Second, RNA vaccines would avoid the barrier function of the nuclear membrane. This is particularly relevant given that antigen expression in non-replicating antigen presenting cells is central to the induction of immunity using nucleic acid vaccines (Ertl and Xiang (1996) supra; Xiang and Ertl (1995) supra; Manickan et al. (1997) supra).

Thus, it is desirable to have an efficient method of delivering RNA to eukaryotic cells, such as mammalian cells, such that, the RNA can be expressed in the eukaryotic cell. Furthermore, it is also desirable to have a system permitting efficient delivery of RNA molecules to mucosal tissue in addition to permitting parenteral delivery of RNA molecules.

SUMMARY OF THE INVENTION

The invention provides a system for delivery of RNA molecules to eukaryotic cells, e.g., cells of mucosal tissue. The invention is based at least in part on the discovery that bacteria which are capable of invading eukaryotic cells can deliver RNA molecules to eukaryotic cells and tissues, and where appropriate, the RNA can be translated if the RNA contains the appropriate regulatory elements.

Accordingly, in one embodiment, the invention provides an isolated bacterium comprising a DNA which is transcribed into a messenger RNA molecule in the bacterium, wherein the RNA is capable of being translated in a eukaryotic cell, or is an antisense RNA or a catalytic RNA. The DNA can be heterologous with respect to the bacterium. The DNA can be operably linked to a prokaryotic promoter, e.g., the *E. coli* NirB promoter. Alternatively, the DNA can be operably linked to a first promoter, and the bacterium further comprises a gene encoding a polymerase, which is capable of mediating transcription from the first promoter, wherein the gene encoding the polymerase is operably linked to a second promoter. In a preferred embodiment the second promoter is a prokaryotic promoter. In a preferred embodiment, the polymerase is a bacteriophage polymerase, e.g., T7 polymerase, and the first promoter is a bacteriophage promoter, e.g., T7 promoter. The DNA which is capable of being transcribed into said RNA and the gene encoding a polymerase can be located on one or more plasmids. However, in a preferred embodiment, the DNA is located on the bacterial chromosome.

In a preferred embodiment, the RNA can be translated in a eukaryotic cell. For allowing efficient translation in a eukaryotic cell, the RNA preferably comprises a Cap Independent Translation Enhancer (CITE) sequence. The RNA can further comprise additional regulatory elements, which can, e.g., affect the stability of the RNA in the eukaryotic cell, e.g., polyA tail. The RNA can encode one polypeptide. Alternatively, the RNA can be polycistronic and encode more than one polypeptide. The polypeptide can be, e.g., a vaccine antigen or an immunoregulatory molecule. The polypeptide can further be an endogenous or a foreign polypeptide. Foreign polypeptides include prokaryotic, e.g., bacterial, or viral polypeptides.

In another preferred embodiment, the RNA is an antisense RNA or a catalytic RNA, e.g., ribozyme. Preferred antisense RNAs or catalytic RNAs are capable of hybridizing to a nucleic acid in the eukaryotic cell, to thereby, e.g., regulate synthesis of a gene product.

In another embodiment, the invention provides an isolated bacterium comprising an RNA which is capable of being translated in a eukaryotic cell, or is an antisense RNA, or a catalytic RNA. In a preferred embodiment, the RNA is transcribed in the bacterium, e.g., from introduced DNA. In another embodiment, the RNA is introduced into the bacterium by, e.g., electroporation. The RNA can be heterologous with respect to the bacterium.

Preferred bacteria of the invention are invasive, i.e., capable of delivering at least one molecule, e.g., an RNA molecule, to a target cell, such as by invading the cytoplasm of the cell. Even more preferred bacteria are live bacteria, e.g., live invasive bacteria. More specifically, preferred bacteria of the invention are those capable of invading a vertebrate cell, e.g., a mammalian cell, such as a cell selected from the group consisting of a human, cattle, sheep, goat, horse, and primate cell.

A preferred invasive bacterium is Shigella, which is naturally invasive vis a vis vertebrate cells. At least one advantage of Shigella RNA vaccine vectors is their tropism for lymphoid tissue in the colonic mucosal surface. In addition, the primary site of Shigella replication is believed to be within dendritic cells and macrophages, which are commonly found at the basal lateral surface of M cells in mucosal lymphoid tissues. Thus, Shigella vectors provide a means to express antigens in these professional antigen presenting cells and thereby induce an immune response, e.g., a vaccine antigen.

Other naturally invasive bacteria include Listeria spp., Rickettsia spp. and enteroinvasive *Escherichia coli*. The term "spp." refers to species of the genus preceding this term. In another embodiment, a bacterium can be modified, such as by genetic engineering means, to increase its invasive potential. In a preferred embodiment, the bacterium has been genetically engineered to mimic the invasion properties of Shigella spp., Listeria spp., Rickettsia spp. and enteroinvasive *Escherichia coli*. Any bacterium can be modified to increase its invasive potential and can be, e.g., a bacterium selected from the group consisting of Yersinia spp., Escherichia spp., Klebsiella spp., Bordetella spp., Neisseria spp., Aeromonas spp., Franciesella spp., Corynebacterium spp., Citrobacter spp., Chlamydia spp., Hemophilus spp., Brucella spp., Mycobacterium spp., Legionella spp., Rhodococcus spp., Pseudomonas spp., Helicobacter spp., Salmonella spp., Vibrio spp., Bacillus spp., Leishmania spp. and Erysipelothrix spp. In another embodiment, the bacterium is modified with an invasion factor, e.g., the bacterium is coated with an invasion factor, e.g., invasin.

The bacterium of the invention is preferably non-harmful to a subject to whom a bacterium of the invention is administered. Accordingly, the bacterium can be a naturally non-pathogenic bacterium. Alternatively, the bacterium can be an attenuated bacterium.

The invention further provides a pharmaceutical composition comprising any of the above-described bacteria and a pharmaceutically acceptable carrier, e.g., a physiological buffer and a lipoprotectant. Such pharmaceutical compositions can be used, e.g., for vaccinating an individual. Also within the scope of the invention are eukaryotic cells, e.g., human cells, comprising any of the above-described bacteria.

The invention also provides isolated DNA operably linked to a prokaryotic promoter, wherein the DNA encodes RNA which is capable of being translated in a eukaryotic cell, or is an antisense RNA or a catalytic RNA, e.g., ribozyme. Preferred prokaryotic promoters are the *E. coli* llp promoter and NirB promoter.

The invention further provides a method for introducing RNA into a eukaryotic cell. According to the invention, a eukaryotic cell is contacted with at least one invasive bacterium comprising a DNA molecule which is either capable of being transcribed into RNA in the bacterium or comprises RNA, wherein the RNA is capable of being translated in a eukaryotic cell or is an antisense RNA or catalytic RNA. The step of contacting the eukaryotic cell with at least one invasive bacterium can be performed in vitro at a multiplicity of infection ranging from about 0.1 to about $10^6$ bacteria per eukaryotic cell. The contacting step is preferably performed in vitro at a multiplicity of infection from about $10^2$ to about $10^4$ bacteria per eukaryotic cell. In one embodiment, the contacting step is performed in vitro, and can, e.g., further comprise the step of administering the eukaryotic cell to a subject. In another preferred embodiment, the contacting step is performed in vivo, and comprises, e.g., administering to a subject the at least one bacterium, but preferably no more than about $10^{11}$ bacteria of the invention. In a preferred embodiment, from about $10^5$ to about $10^9$ bacteria are administered to a subject. The bacteria can be administered, e.g., orally, intrarectally, or intranasally to the subject. The bacterium can also be administered parenterally.

The invasive bacterium can be cell type specific. Alternatively, the invasive bacterium can be capable of invading one or more cell types. The invasive bacterium can also be modified to change its target specificity, e.g., by genetic engineering and/or by linking a specific targeting factor to the bacterium. In yet another embodiment, a non-invasive bacterium is be modified to become invasive. The bacterium can also be modified by engineering the bacterium to contain a suicide gene.

The eukaryotic cell to which the bacterium of the invention is targeted can be any type of cell. A preferred cell is from a mucosal tissue. In one embodiment, the cell is a natural target of the bacterium. In another embodiment, the target cell is modified, e.g., genetically, to contain a surface receptor necessary for mediating the interaction between the bacterium and the target cell.

Thus, the method of the invention retains all the advantages and properties of introducing RNA into a eukaryotic cell and provides a more efficient manner to deliver the RNA to the target eukaryotic cell. The advantages of introducing RNA into a eukaryotic cell instead of a DNA molecule include (i) avoidance of risk of insertion of DNA into the genome of the target eukaryotic cell and thus strongly reduced risk of mutation of the target eukaryotic cell; (ii) absence of need for the nucleic acid introduced in the eukaryotic cell to traverse the nuclear membrane; and (iii) avoidance of the possibility of shedding of plasmid molecules from the bacteria. Delivery of RNA to eukaryotic cells by use of a bacterium, compared to delivery of "naked" RNA, e.g., where expression of the RNA is desired, provides at least the advantage that the RNA is protected and less likely to be degraded prior to entering the eukaryotic cell. Furthermore, the RNA can be specifically targeted to certain types of cells, since the bacterium can naturally target or be modified to target specific types of cells, e.g., antigen presenting cells in the mucosal lymphoid tissue.

Furthermore, the invention provides methods and compositions for oral vaccines, in particular, for an oral mucosal HIV-1 vaccine. Historically, oral vaccines have proven to be an efficacious means to invoke mucosal immunity. The invention provides oral vaccines using Shigella bacteria, which possess specialized adaptations that allow this organism to invade and replicate in the cytoplasm of antigen presenting cells associated with the colonic lymphoid tissue, thus eliciting strong immune responses. Thus, the invention provides efficacious oral vaccines.

Other features and advantages of the invention will be apparent from the following detailed description and claims.

BRIEF DESCRIPTION OF THE FIGURES

FIG. 1 (SEQ ID NO: 1) shows a nucleotide sequence of a CITE sequence from the encephalomyocarditis virus (ECMV) 5' non-coding region.

DETAILED DESCRIPTION OF THE INVENTION

Figure 2:
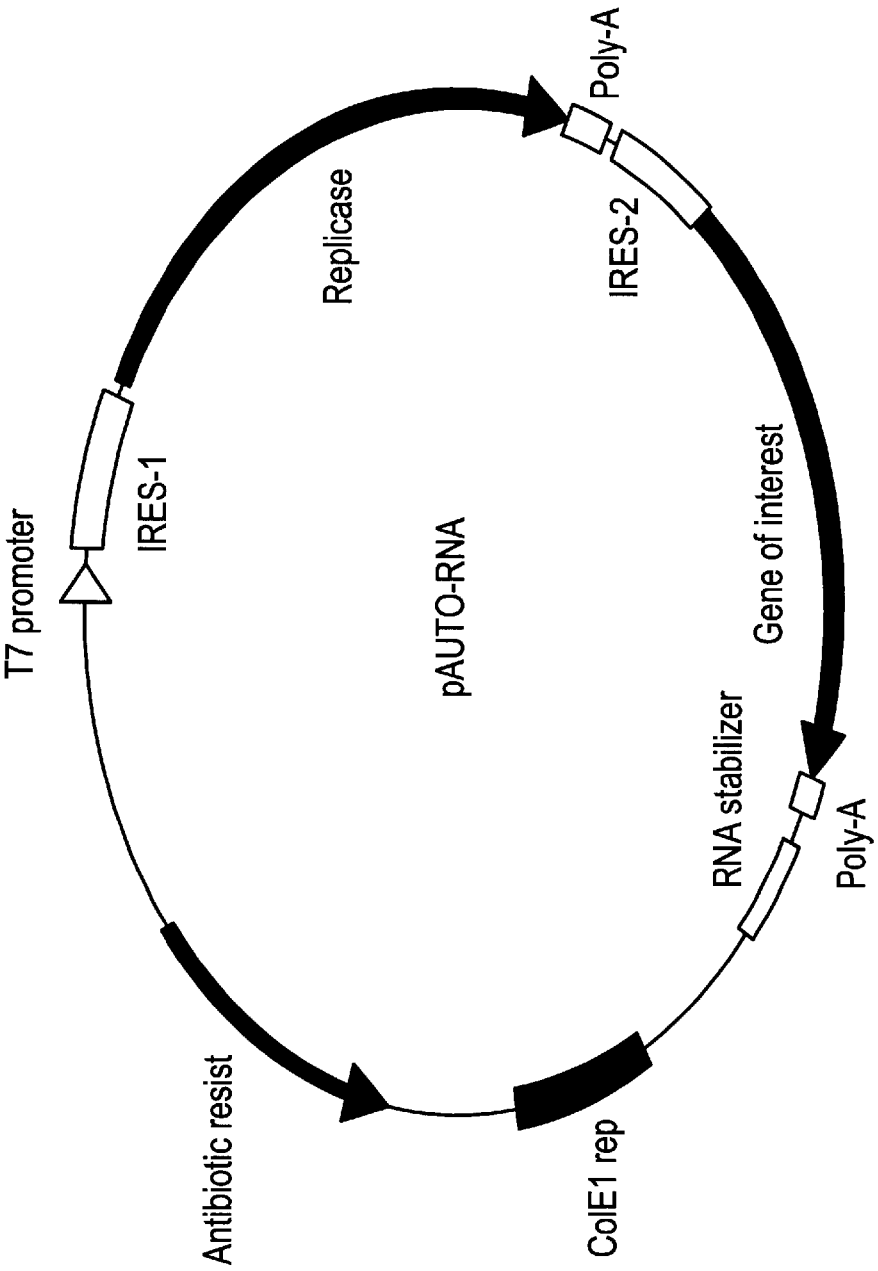
FIG. 2 is a diagram of auto-amplified RNA for cytoplasmic expression of a target gene.

The invention is based at least in part on the discovery that bacteria, which are capable of invading eukaryotic cells, can deliver RNA to eukaryotic cells. Furthermore, if the RNA contains the necessary eukaryotic translation recognition elements, the RNA can be efficiently translated in the eukaryotic cell to which the RNA was delivered by the bacterium. Accordingly, in one embodiment, the invention provides a bacterium comprising DNA which is capable of being transcribed into RNA in the bacterium, wherein the RNA is capable of being translated in a eukaryotic cell, or is an antisense RNA or a catalytic RNA.

In a preferred embodiment, the invention provides a mucosal RNA bacterial vector, capable of efficiently delivering RNA to mucosal cells. Such RNA bacterial vectors are useful as vaccines since they can be administered orally and will be targeted to sites which are rich in professional antigen presenting cells, e.g, macrophages and dendritic cells, thus eliciting a strong immune response to the vaccine antigen. Thus, the invention provides live oral bacterial vaccine vectors.

1. Bacteria Delivering RNA to Eukaryotic Cells

According to the invention, any microorganism which is capable of delivering a molecule, e.g., an RNA molecule, into the cytoplasm of a target cell, such as by traversing the membrane and entering the cytoplasm of a cell, can be used to deliver RNA to such cells. In a preferred embodiment, the microorganism is a prokaryote. In an even more preferred embodiment, the prokaryote is a bacterium. Also within the scope of the invention are microorganisms other than bacteria which can be used for delivering RNA to a cell. For example, the microorganism can be a fungus, e.g., *Cryptococcus neoformans,* protozoan, e.g., *Trypanosoma cruzi, Toxoplasma gondii, Leishmania donovani,* and plasmodia. In certain embodiments, the mircroorganism is a virus.

As used herein, the term "invasive" when referring to a microorganism, e.g., a bacterium, refers to a microorganism which is capable of delivering at least one molecule, e.g., an RNA molecule, to a target cell. An invasive microorganism can be a microorganism which is capable of traversing a cell membrane, thereby entering the cytoplasm of said cell, and delivering at least some of its content, e.g., RNA, into the target cell. The process of delivery of the at least one molecule into the target cell preferably does not significantly modify the invasion apparatus.

In a preferred embodiment, the microorganism is a bacterium. A preferred invasive bacterium is a bacterium which is capable of delivering at least one molecule, e.g., an RNA molecule, to a target cells, such as by entering the cytoplasm of a eukaryotic cell. Preferred invasive bacteria are live bacteria, e.g., live invasive bacteria.

Invasive microorganisms include microorganisms that are naturally capable of delivering at least one molecule to a target cell, such as by traversing the cell membrane, e.g., a eukaryotic cell membrane, and entering the cytoplasm, as well as microorganisms which are not naturally invasive and which have been modified, e.g., genetically modified, to be invasive. In another preferred embodiment, a microorganism which is not naturally invasive can be modified to become invasive by linking the bacterium to an "invasion factor", also termed "entry factor" or "cytoplasm-targeting factor". As used herein, an "invasion factor" is a factor, e.g., a protein, which, when expressed by a non-invasive bacterium, renders the bacterium invasive. As used herein, an "invasion factor" is encoded by a "cytoplasm-targeting gene".

Naturally invasive microorganisms, e.g., bacteria, may have a certain tropism, i.e., preferred target cells. Alternatively, microorganisms, e.g., bacteria can be modified, e.g., genetically, to mimic the tropism of a second microorganism.

Delivery of at least one molecule into a target cell can be determined according to methods known in the art. For example, the presence of the molecule, such as an RNA molecule or polypeptide encoded thereby, can be detected by hybridization or PCR methods, or by immunological methods which may include the use of an antibody.

Determining whether a microorganism is sufficiently invasive for use in the invention may include determining whether sufficient RNA, or polypeptide encoded thereby, was delivered to host cells, relative to the number of microorganisms contacted with the host cells. If the amount of RNA, or polypeptide encoded thereby, is low relative to the number of microorganisms used, it may be desirable to further modify the microorganism to increase its invasive potential.

Bacterial entry into cells can be measured by various methods. Intracellular bacteria survive treatment by aminoglycoside antibiotics, whereas extracellular bacteria are rapidly killed. A quantitative estimate of bacterial uptake can be achieved by treating cell monolayers with the antibiotic gentamicin to inactivate extracellular bacteria, then by removing said antibiotic before liberating the surviving intracellular organisms with gentle detergent and determining viable counts on standard bacteriological medium. Furthermore, bacterial entry into cells can be directly observed, e.g., by thin-section-transmission electron microscopy of cell layers or by immunofluorescent techniques (Falkow et al. (1992) *Annual Rev. Cell Biol.* 8:333). Thus, various techniques can be used to determine whether a specific bacteria is capable of invading a specific type of cell or to confirm bacterial invasion following modification of the bacteria, such modification of the tropism of the bacteria to mimic that of a second bacterium.

Bacteria that can be used for delivering RNA according to the method of the invention are preferably non-pathogenic. However, pathogenic bacteria can also be used, so long as their pathogenicity has been attenuated, to thereby render the bacteria non-harmful to a subject to which it is administrated. As used herein, the term "attenuated bacterium" refers to a bacterium that has been modified to significantly reduce or eliminate its harmfulness to a subject. A pathogenic bacterium can be attenuated by various methods, set forth below.

Without wanting to be limited to a specific mechanism of action, the bacterium delivering the RNA into the eukaryotic cell can enter various compartments of the cell, depending on the type of bacterium. For example, the bacterium can be in a vesicle, e.g., a phagocytic vesicle. Once inside the cell, the bacterium can be destroyed or lysed and its contents delivered to the eukaryotic cell. A bacterium can also be engineered to express a phagosome degrading enyzme to allow leakage of RNA from the phagosome. In some embodiments, the bacterium can stay alive for various times in the eukaryotic cell and may continue to produce RNA. The RNA can then be released from the bacterium into the cell by, e.g., leakage. In certain embodiments of the invention, the bacterium can also replicate in the eukaryotic cell. In a preferred embodiment, bacterial replication does not kill the host cell. The invention is not limited to delivery of RNA by a specific mechanism and is intended to encompass methods and compositions permitting delivery of RNA by a bacterium independently of the mechanism of delivery of the RNA.

Set forth below are examples of bacteria which have been described in the literature as being naturally invasive (section 1.1), as well as bacteria which have been described in the literature as being naturally non-invasive bacteria (section 1.2), as well as bacteria which are naturally non-pathogenic or which are attenuated. Although some bacteria have been described as being non-invasive (section 1.2), these may still be sufficiently invasive for use according to the invention. Whether traditionally described as naturally invasive or non-invasive, any bacterial strain can be modified to modulate, in particular to increase, its invasive characteristics (e.g., as described in section 1.3).

1.1 Naturally Invasive Bacteria

The particular naturally invasive bacteria employed in the present invention is not critical thereto. Examples of such naturally-occurring invasive bacteria include, but are not limited to, Shigella spp., Salmonella spp., Listeria spp., Rickettsia spp., and enteroinvasive *Escherichia coli*.

The particular Shigella strain employed is not critical to the present invention. Examples of Shigella strains which can be employed in the present invention include *Shigella flexneri* 2a (ATCC No. 29903), *Shigella sonnei* (ATCC No. 29930), and *Shigella disenteriae* (ATCC No. 13313). An attenuated Shigella strain, such as *Shigella flexneri* 2a 2457T aroA virG mutant CVD 1203 (Noriega et al, supra), *Shigella flexneri* M90T icsA mutant (Goldberg et al, *Infect. Immun.*, 62:5664–5668 (1994)), *Shigella flexneri* Y SFL114 aroD mutant (Karnell et al, *Vacc.*, 10:167–174 (1992)), and *Shigella flexneri* aroA aroD mutant (Verma et al, *Vacc.*, 9:6–9 (1991)) are preferably employed in the present invention. Alternatively, new attenuated Shigella spp. strains can be constructed by introducing an attenuating mutation either singularly or in conjunction with one or more additional attenuating mutations.

At least one advantage to Shigella RNA vaccine vectors is their tropism for lymphoid tissue in the colonic mucosal surface. In addition, the primary site of Shigella replication is believed to be within dendritic cells and macrophages, which are commonly found at the basal lateral surface of M cells in mucosal lymphoid tissues (reviewed by McGhee, J. R. et al. (1994) *Reproduction, Fertility, & Development* 6:369; Pascual, D. W. et al. (1994) *Immunomethods* 5:56). As such, Shigella vectors may provide a means to express antigens in these professional antigen presenting cells. Another advantage of Shigella vectors is that attenuated Shigella strains deliver nucleic acid reporter genes in vitro and in vivo (Sizemore, D. R. et al. (1995) *Science* 270:299; Courvalin, P. et al. (1995) *Comptes Rendus de l Academie des Sciences Serie III-Sciences de la Vie-Life Sciences* 318:1207; Powell, R. J. et al. (1996) In: Molecular approaches to the control of infectious diseases. F. Brown, E. Norrby, D. Burton and J. Mekalanos, eds. Cold Spring Harbor Laboratory Press, New York. 183; Anderson, R. J. et al. (1997) *Abstracts for the 97th General Meeting of the American Society for Microbiology*:E.). On the practical side, the tightly restricted host specificity of Shigella stands to prevent the spread of Shigella vectors into the food chain via intermediate hosts. Furthermore, attenuated strains that are highly attenuated in rodents, primates and volunteers have been developed (Anderson et al. (1997) supra; Li, A. et al. (1992) *Vaccine* 10:395; Li, A. et al. (1993) *Vaccine* 11:180; Karnell, A. et al. (1995) *Vaccine* 13:88; Sansonetti, P. J. and J. Arondel (1989) *Vaccine* 7:443; Fontaine, A. et al. (1990) *Research in Microbiology* 141:907; Sansonetti, P. J. et al. (1991) *Vaccine* 9:416; Noriega, F. R. et al. (1994) *Infection & Immunity* 62:5168; Noriega, F. R. et al. (1996) *Infection & Immunity* 64:3055; Noriega, F. R. et al. (1996) *Infection & Immunity* 64:23; Noriega, F. R. et al. (1996) *Infection & Immunity* 64:3055; Kotloff, K. L. et al. (1996) *Infection & Immunity* 64:4542). This latter knowledge will allow the development of well tolerated Shigella vectors for use in humans.

Attenuating mutations can be introduced into bacterial pathogens using non-specific mutagenesis either chemically, using agents such as N-methyl-N'-nitro-N-nitrosoguanidine, or using recombinant DNA techniques; classic genetic techniques, such as Tn10 mutagenesis, P22-mediated transduction, λ phage mediated crossover, and conjugational transfer; or site-directed mutagenesis using recombinant DNA techniques. Recombinant DNA techniques are preferable since strains constructed by recombinant DNA techniques are far more defined. Examples of such attenuating mutations include, but are not limited to:

(i) auxotrophic mutations, such as aro (Hoiseth et al, *Nature*, 291:238–239 (1981)), gua (McFarland et al, *Microbiol. Path.*, 3:129–141 (1987)), nad (Park et al, *J. Bact.*, 170:3725–3730 (1988), thy (Nnalue et al, *Infect. Immun.*, 55:955–962 (1987)), and asd (Curtiss, supra) mutations;

(ii) mutations that inactivate global regulatory functions, such as cya (Curtiss et al, *Infect. Immun.,* 55:3035–3043 (1987)), crp (Curtiss et al (1987), supra), phoP/phoQ (Groisman et al, *Proc. Natl. Acad. Sci., USA,* 86:7077–7081 (1989); and Miller et al, *Proc. Natl. Acad. Sci., USA,* 86:5054–5058 (1989)), phop$^c$ (Miller et al, *J. Bact.,* 172:2485–2490 (1990)) or ompR (Dorman et al, *Infect. Immun.,* 57:2136–2140 (1989)) mutations;

(iii) mutations that modify the stress response, such as recA (Buchmeier et al, *Mol. Micro.,* 7:933–936 (1993)), htrA (Johnson et al, *Mol. Micro.,* 5:401–407 (1991)), htpR (Neidhardt et al, *Biochem. Biophys. Res. Com.,* 100:894–900 (1981)), hsp (Neidhardt et al, *Ann. Rev. Genet.,* 18:295–329 (1984)) and groEL (Buchmeier et al, *Sci.,* 248:730–732 (1990)) mutations;

(iv) mutations in specific virulence factors, such as IsyA (Libby et al, *Proc. Natl. Acad. Sci., USA,* 91:489–493 (1994)), pag or prg (Miller et al (1990), supra; and Miller et al (1989), supra), iscA or virG (d'Hauteville et al, *Mol. Micro.,* 6:833–841 (1992)), plcA (Mengaud et al, *Mol. Microbiol.,* 5:367–72 (1991); Camilli et al, *J. Exp. Med,* 173:751–754 (1991)), and act (Brundage et al, *Proc. Natl. Acad. Sci., USA,* 90:11890–11894 (1993)) mutations;

(v) mutations that affect DNA topology, such as topA (Galan et al, *Infect. Immun.,* 58:1879–1885 (1990));

(vi) mutations that disrupt or modify the cell cycle, such as min (de Boer et al, *Cell,* 56:641–649 (1989)).

(vii) introduction of a gene encoding a suicide system, such as sacB (Recorbet et al, *App. Environ. Micro.,* 59:1361–1366 (1993); Quandt et al, *Gene,* 127:15–21 (1993)), nuc (Ahrenholtz et al, *App. Environ. Micro.,* 60:3746–3751 (1994)), hok, gef, kil, or phlA (Molin et al, *Ann. Rev. Microbiol.,* 47:139–166 (1993));

(viii) mutations that alter the biogenesis of lipopolysaccharide and/or lipid A, such as rFb (Raetz in *Esherishia coli* and *Salmonella typhimurium,* Neidhardt et al., Ed., ASM Press, Washington D.C. pp 1035–1063 (1996)), galE (Hone et al, *J. Infect. Dis.,* 156:164–167 (1987)) and htrB (Raetz, supra), msbB (Reatz, supra)

(ix) introduction of a bacteriophage lysis system, such as lysogens encoded by P22 (Rennell et al, *Virol,* 143:280–289 (1985)), λ murein transglycosylase (Bienkowska-Szewczyk et al, *Mol. Gen. Genet.,* 184:111–114 (1981)) or S-gene (Reader et al, *Virol,* 43:623–628 (1971)); and The attenuating mutations can be either constitutively expressed or under the control of inducible promoters, such as the temperature sensitive heat shock family of promoters (Neidhardt et al, supra), or the anaerobically induced nirB promoter (Harborne et al, *Mol. Micro.,* 6:2805–2813 (1992)) or repressible promoters, such as uapA (Gorfinkiel et al, *J. Biol. Chem.,* 268:23376–23381 (1993)) or gcv (Stauffer et al, *J. Bact.,* 176:6159–6164 (1994)).

The particular Listeria strain employed is not critical to the present invention. Examples of Listeria strains which can be employed in the present invention include *Listeria monocytogenes* (ATCC No. 15313). Attenuated Listeria strains, such as *L. monocytogenes* actA mutant (Brundage et al, supra) or *L. monocytogenes* plcA (Camilli et al, *J. Exp. Med.,* 173:751–754 (1991)) are preferably used in the present invention. Alternatively, new attenuated Listeria strains can be constructed by introducing one or more attenuating mutations in groups (i) to (vii) as described for Shigella spp. above.

The particular Salmonella strain employed is not critical to the present invention. Examples of Salmonella strains which can be employed in the present invention include *Salmonella typhi* (ATCC No. 7251) and *S. typhimurium* (ATCC No. 13311). Attenuated Salmonella strains are preferably used in the present invention and include *S. typhi*-aroC-aroD (Hone et al. Vacc. 9:810 (1991) and *S. typhimurium*-aroA mutant (Mastroeni et al. Micro. Pathol. 13:477 (1992)). Alternatively, new attenuated Salmonella strains can be constructed by introducing one or more attenuating mutations as described fro Shigella spp. above.

The particular Rickettsia strain employed is not critical to the present invention. Examples of Rickettsia strains which can be employed in the present invention include *Rickettsia rickettsiae* (ATCC Nos. VR149 and VR891), *Ricketsia prowaseckii* (ATCC No. VR233), *Rickettsia tsutsugamuchi* (ATCC Nos. VR312, VR150 and VR609), *Rickettsia mooseri* (ATCC No. VR144), *Rickettsia sibirica* (ATCC No. VR151), and *Rochalimaea quitana* (ATCC No. VR358). Attenuated Rickettsia strains are preferably used in the present invention and can be constructed by introducing one or more attenuating mutations in groups (i) to (vii) as described for Shigella spp. above.

The particular enteroinvasive Escherichia strain employed is not critical to the present invention. Examples of enteroinvasive Escherichia strains which can be employed in the present invention include *Escherichia coli* strains 4608-58, 1184-68, 53638-C-17, 13-80, and 6-81 (Sansonetti et al, *Ann. Microbiol. (Inst. Pasteur),* 132A:351–355 (1982)). Attenuated enteroinvasive Escherichia strains are preferably used in the present invention and can be constructed by introducing one or more attenuating mutations in groups (i) to (vii) as described for Shigella spp. above.

Furthermore, since certain microorganisms other than bacteria can also interact with integrin molecules (which are receptors for certain invasion factors) for cellular uptake, such microorganisms can also be used for introducing RNA into target cells. For example, viruses, e.g., foot-and-mouth disease virus, echovirus, and adenovirus, and eukaryotic pathogens, e.g., Histoplasma capsulatum and Leishmania major interact with integrin molecules.

1.2 Less Invasive Bacteria

Examples of bacteria which can be used in the invention and which have been described in the literature as being non-invasive or at least less invasive than the bacteria listed in the previous section (1.1) include, but are not limited to, Yersinia spp., Escherichia spp., Klebsiella spp., Bordetella spp., Neisseria spp., Aeromonas spp., Franciesella spp., Corynebacterium spp., Citrobacter spp., Chlamydia spp., Hemophilus spp., Brucella spp., Mycobacterium spp., Legionella spp., Rhodococcus spp., Pseudomonas spp., Helicobacter spp., Vibrio spp., Bacillus spp., and Erysipelothrix spp. It may be necessary to modify these bacteria to increase their invasive potential.

The particular Yersinia strain employed is not critical to the present invention. Examples of Yersinia strains which can be employed in the present invention include *Y. enterocolitica* (ATCC No. 9610) or *Y. pestis* (ATCC No. 19428). Attenuated Yersinia strains, such as *Y. enterocolitica* Ye03-R2 (al-Hendy et al, *Infect. Immun.,* 60:870–875 (1992)) or *Y. enterocolitica* aroA (O'Gaora et al, *Micro. Path.,* 9:105–116 (1990)) are preferably used in the present invention. Alternatively, new attenuated Yersinia strains can be constructed by introducing one or more attenuating mutations in groups (i) to (vii) as described for Shigella spp. above.

The particular Escherichia strain employed is not critical to the present invention. Examples of Escherichia strains which can be employed in the present invention include *E. coli* H10407 (Elinghorst et al, *Infect. Immun.*, 60:2409–2417 (1992)), and *E. coli* EFC4, CFT325 and CPZ005 (Donnenberg et al, *J. Infect. Dis.*, 169:831–838 (1994)). Attenuated Escherichia strains, such as the attenuated turkey pathogen *E. coli* 02 carAB mutant (Kwaga et al, *Infect. Immun.*, 62:3766–3772 (1994)) are preferably used in the present invention. Alternatively, new attenuated Escherichia strains can be constructed by introducing one or more attenuating mutations in groups (i) to (vii) as described for Shigella spp. above.

The particular Klebsiella strain employed is not critical to the present invention. Examples of Klebsiella strains which can be employed in the present invention include *K. pneumoniae* (ATCC No. 13884). Attenuated Klebsiella strains are preferably used in the present invention, and can be constructed by introducing one or more attenuating mutations in groups (i) to (vii) as described for Shigella spp. above.

The particular Bordetella strain employed is not critical to the present invention. Examples of Bordetella strains which can be employed in the present invention include *B. bronchiseptica* (ATCC No. 19395). Attenuated Bordetella strains are preferably used in the present invention, and can be constructed by introducing one or more attenuating mutations in groups (i) to (vii) as described for Shigella spp. above.

The particular Neisseria strain employed is not critical to the present invention. Examples of Neisseria strains which can be employed in the present invention include *N. meningitidis* (ATCC No. 13077) and *N. gonorrhoeae* (ATCC No. 19424). Attenuated Neisseria strains, such as *N. gonorrhoeae* MS11 aro mutant (Chamberlain et al, *Micro. Path.*, 15:51–63 (1993)) are preferably used in the present invention. Alternatively, new attenuated Neisseria strains can be constructed by introducing one or more attenuating mutations in groups (i) to (vii) as described for Shigella spp. above.

The particular Aeromonas strain employed is not critical to the present invention. Examples of Aeromonas strains which can be employed in the present invention include *A. eucrenophila* (ATCC No. 23309). Alternatively, new attenuated Aeromonas strains can be constructed by introducing one or more attenuating mutations in groups (i) to (vii) as described for Shigella spp. above.

The particular Franciesella strain employed is not critical to the present invention. Examples of Franiesella strains which can be employed in the present invention include *F. tularensis* (ATCC No. 15482). Attenuated Franciesella strains are preferably used in the present invention, and can be constructed by introducing one or more attenuating mutations in groups (i) to (vii) as described for Shigella spp. above.

The particular Corynebacterium strain employed is not critical to the present invention. Examples of Corynebacterium strains which can be employed in the present invention include *C. pseudotuberculosis* (ATCC No. 19410). Attenuated Corynebacterium strains are preferably used in the present invention, and can be constructed by introducing one or more attenuating mutations in groups (i) to (vii) as described for Shigella spp. above.

The particular Citrobacter strain employed is not critical to the present invention. Examples of Citrobacter strains which can be employed in the present invention include *C. freundii* (ATCC No. 8090). Attenuated Citrobacter strains are preferably used in the present invention, and can be constructed by introducing one or more attenuating mutations in groups (i) to (vii) as described for Shigella spp. above.

The particular Chlamydia strain employed is not critical to the present invention. Examples of Chlamydia strains which can be employed in the present invention include *C. pneumoniae* (ATCC No. VR1310). Attenuated Chlamydia strains are preferably used in the present invention, and can be constructed by introducing one or more attenuating mutations in groups (i) to (vii) as described for Shigella spp. above.

The particular Hemophilus strain employed is not critical to the present invention. Examples of Hemophilus strains which can be employed in the present invention include *H. sornnus* (ATCC No. 43625). Attenuated Hemophilus strains are preferably used in the present invention, and can be constructed by introducing one or more attenuating mutations in groups (i) to (vii) as described for Shigella spp. above.

The particular Brucella strain employed is not critical to the present invention. Examples of Brucella strains which can be employed in the present invention include *B. abortus* (ATCC No. 23448). Attenuated Brucella strains are preferably used in the present invention, and can be constructed by introducing one or more attenuating mutations in groups (i) to (vii) as described for Shigella spp. above.

The particular Mycobacterium strain employed is not critical to the present invention. Examples of Mycobacterium strains which can be employed in the present invention include *M. intracellulare* (ATCC No. 13950) and *M. tuberculosis* (ATCC No. 27294). Attenuated Mycobacterium strains are preferably used in the present invention, and can be constructed by introducing one or more attenuating mutations in groups (i) to (vii) as described for Shigella spp. above.

The particular Legionella strain employed is not critical to the present invention. Examples of Legionella strains which can be employed in the present invention include *L. pneumophila* (ATCC No. 33156). Attenuated Legionella strains, such as a *L. pneumophila* mip mutant (Ott, *FEMS Micro. Rev.,* 14:161–176 (1994)) are preferably used in the present invention. Alternatively, new attenuated Legionella strains can be constructed by introducing one or more attenuating mutations in groups (i) to (vii) as described for Shigella spp. above.

The particular Rhodococcus strain employed is not critical to the present invention. Examples of Rhodococcus strains which can be employed in the present invention include *R. equi* (ATCC No. 6939). Attenuated Rhodococcus strains are preferably used in the present invention, and can be constructed by introducing one or more attenuating mutations in groups (i) to (vii) as described for Shigella spp. above.

The particular Pseudomonas strain employed is not critical to the present invention. Examples of Pseudomonas strains which can be employed in the present invention include *P. aeruginosa* (ATCC No. 23267). Attenuated Pseudomonas strains are preferably used in the present invention, and can be constructed by introducing one or more attenuating mutations in groups (i) to (vii) as described for Shigella spp. above.

The particular Helicobacter strain employed is not critical to the present invention. Examples of Helicobacter strains which can be employed in the present invention include *H. mustelae* (ATCC No. 43772). Attenuated Helicobacter strains are preferably used in the present invention, and can be constructed by introducing one or more attenuating mutations in groups (i) to (vii) as described for Shigella spp. above.

The particular Salmonella strain employed is not critical to the present invention. Examples of Salmonella strains which can be employed in the present invention include *Salmonella typhi* (ATCC No. 7251) and *S. typhimurium* (ATCC No. 13311). Attenuated Salmonella strains are preferably used in the present invention and include *S. typhi* aroC aroD (Hone et al, *Vacc.,* 9:810–816 (1991)) and *S. typhimurium* aroA mutant (Mastroeni et al, *Micro. Pathol,* 13:477–491 (1992))). Alternatively, new attenuated Salmonella strains can be constructed by introducing one or more attenuating mutations in groups (i) to (vii) as described for Shigella spp. above.

The particular Vibrio strain employed is not critical to the present invention. Examples of Vibrio strains which can be employed in the present invention include *Vibrio cholerae* (ATCC No. 14035) and *Vibrio cincinnatiensis* (ATCC No. 35912). Attenuated Vibrio strains are preferably used in the present invention and include *V. cholerae* RSI virulence mutant (Taylor et al, *J. Infect. Dis.,* 170:1518–1523 (1994)) and *V. cholerae* ctxA, ace, zot, cep mutant (Waldor et al, *J. Infect. Dis.,* 170:278–283 (1994)). Alternatively, new attenuated Vibrio strains can be constructed by introducing one or more attenuating mutations in groups (i) to (vii) as described for Shigella spp. above.

The particular Bacillus strain employed is not critical to the present invention. Examples of Bacillus strains which can be employed in the present invention include *Bacillus subtilis* (ATCC No. 6051). Attenuated Bacillus strains are preferably used in the present invention and include *B. anthracis* mutant pX01 (Welkos et al, *Micro. Pathol,* 14:381–388 (1993)) and attenuated BCG strains (Stover et al, *Nat.,* 351:456–460 (1991)). Alternatively, new attenuated Bacillus strains can be constructed by introducing one or more attenuating mutations in groups (i) to (vii) as described for Shigella spp. above.

The particular Erysipelothrix strain employed is not critical to the present invention. Examples of Erysipelothrix strains which can be employed in the present invention include *Erysipelothrix rhusiopathiae* (ATCC No. 19414) and *Erysipelothrix tonsillarum* (ATCC No. 43339). Attenuated Erysipelothrix strains are preferably used in the present invention and include *E. rhusiopathiae* Kg-1a and Kg-2 (Watarai et al, *J. Vet. Med. Sci.,* 55:595–600 (1993)) and *E. rhusiopathiae* ORVAC mutant (Markowska-Daniel et al, *Int. J. Med. Microb. Virol. Parisit. Infect. Dis.,* 277:547–553 (1992)). Alternatively, new attenuated Erysipelothrix strains can be constructed by introducing one or more attenuating mutations in groups (i) to (vii) as described for Shigella spp. above.

1.3. Methods for Increasing the Invasive Properties of a Bacterial Strain

Whether organisms have been traditionally described as invasive or non-invasive, these organisms can be engineered to increase their invasive properties, e.g., by mimicking the invasive properties of Shigella spp., Listeria spp., Rickettsia spp., or enteroinvasive *E. coli* spp. For example, one or more genes that enable the microorganism to access the cytoplasm of a cell, e.g., a cell in the natural host of said non-invasive bacteria, can be introduced into the microorganism.

Examples of such genes referred to herein as "cytoplasm-targeting genes" include genes encoding the proteins that enable invasion by Shigella or the analogous invasion genes of entero-invasive Escherichia, or listeriolysin O of Listeria, as such techniques are known to result in rendering a wide array of invasive bacteria capable of invading and entering the cytoplasm of animal cells (Formal et al, *Infect. Immun.,* 46:465 (1984); Bielecke et al, *Nature,* 345:175–176 (1990); Small et al, In: *Microbiology*-1986, pages 121–124, Levine et al, Eds., American Society for Microbiology, Washington, D.C. (1986); Zychlinsky et al, *Molec. Micro.,* 11:619–627 (1994); Gentschev et al. (1995) *Infection & Immunity* 63:4202; Isberg, R. R. and S. Falkow (1985) *Nature* 317:262; and Isberg, R. R. et al. (1987) Cell 50:769). Methods for transferring the above cytoplasm-targeting genes into a bacterial strain are well known in the art. Another preferred gene which can be introduced into bacteria to increase their invasive character encodes the invasin protein from *Yersinia pseudotuberculosis,* (Leong et al. *EMBO J.,* 9:1979 (1990)). Invasin can also be introduced in combination with listeriolysin, thereby further increasing the invasive character of the bacteria relative to the introduction of either of these genes. The above genes have been described for illustrative purposes; however, it will be obvious to those skilled in the art that any gene or combination of genes, from one or more sources, that participates in the delivery of a molecule, in particular an RNA molelecule, from a microorganism into the cytoplasm of a cell, e.g., an animal cell, will suffice. Thus, such genes are not limited to bacterial genes, and include viral genes, such as influenza virus hemagglutinin HA-2 which promotes endosmolysis (Plank et al, *J. Biol. Chem.,* 269:12918–12924 (1994)).

The above cytoplasm-targeting genes can be obtained by, e.g., PCR amplification from DNA isolated from an invasive bacterium carrying the desired cytoplasm-targeting gene. Primers for PCR can be designed from the nucleotide sequences available in the art, e.g., in the above-listed references and/or in GenBank, which is publically available on the internet (www.ncbi.nlm.nih.gov/). The PCR primers can be designed to amplify a cytoplasm-targeting gene, a cytoplasm-targeting operon, a cluster of cytoplasm-targeting genes, or a regulon of cytoplasm-targeting genes. The PCR strategy employed will depend on the genetic organization of the cytoplasm-targeting gene or genes in the target invasive bacteria. The PCR primers are designed to contain a sequence that is homologous to DNA sequences at the beginning and end of the target DNA sequence. The cytoplasm-targeting genes can then be introduced into the target bacterial strain, e.g., by using Hfr transfer or plasmid mobilization (Miller, *A Short Course in Bacterial Genetics,* Cold Spring Harbor Laboratory Press, Cold Spring Harbor, N.Y. (1992); Bothwell et al, supra; and Ausubel et al, supra), bacteriophage-mediated transduction (de Boer, supra; Miller, supra; and Ausubel et al, supra), chemical transformation (Bothwell et al, supra; Ausubel et al, supra), electroporation (Bothwel et al, supra; Ausubel et al, supra; and Sambrook, *Molecular Cloning: A Laboratory Manual,* Cold Spring Harbor Laboratory Press, Cold Spring Harbor, N.Y.) and physical transformation techniques (Johnston et al, supra; and Bothwell, supra). The cytoplasm-targeting genes can be incorporated into lysogenic bacteriophage (de Boer et al, *Cell,* 56:641–649 (1989)), plasmids vectors (Curtiss et al, supra) or spliced into the chromosome (Hone et al, supra) of the target strain.

In addition to genetically engineering bacteria to increase their invasive properties, as set forth above, bacteria can also be modified by linking an invasion factor to the bacteria. Accordingly, in one embodiment, a bacterium is rendered more invasive by coating the bacterium, either covalently or non-covalently, with an invasion factor, e.g., the protein invasin, invasin derivatives, or a fragment thereof sufficient for invasiveness. In fact, it has been shown that non-invasive bacterial cells coated with purified invasin from *Yersinia pseudotuberculosis* or the carboxyl-terminal 192 amino acids of invasin are able to enter mammalian cells (Leong et al. (1990) EMBO J. 9:1979). Furthermore, latex beads coated with the carboxyl terminal region of invasin are efficiently internalized by mammalian cells, as are strains of *Staphylococcus aureus* coated with antibody-immobilized invasin (reviewed in Isberg and Tran van Nhieu (1994) *Ann. Rev. Genet.* 27:395). Alternatively, a bacterium can also be coated with an antibody, variant thereof, or fragment thereof which binds specifically to a surface molecule recognized by a bacterial entry factor. For example, it has been shown that bacteria are internalized if they are coated with a monoclonal antibody directed against an integrin molecule, e.g., α5β1, known to be the surface molecule with which the bacterial invasin protein interacts (Isberg and Tran van Nhieu, supra). Such antibodies can be prepared according to methods known in the art. The antibodies can be tested for efficacy in mediating bacterial invasiveness by, e.g., coating bacteria with the antibody, contacting the bacteria with eukaryotic cells having a surface receptor recognized by the antibody, and monitoring the presence of intracellular bacteria, according to the methods described above. Methods for linking an invasion factor to the surface of a bacterium are known in the art and include cross-linking.

Bacteria can also be modified genetically to express an antibody, or variant thereof, or other factor capable of binding specifically to a receptor of an invasion factor, e.g., an integrin molecule. Antibody genes can be isolated according to methods known in the art. Furthermore, to reduce an immune reaction of the host towards the antibody, it may be desirable to use humanized antibodies. Such antibodies can be prepared as described in U.S. Pat. No. 5,585,089. Accordingly, the invention encompasses any bacterium modified, either genetically or otherwise, to have on its surface a factor, e.g., antibody, binding specifically to a receptor of an invasion factor, said bacterium being capable of delivering RNA to a eukaryotic cell.

2. Target Cells

The invention provides a method for delivering RNA to any type of target cell. As used herein, the term "target cell" refers to a cell which can be invaded by a bacterium, i.e., a cell which has the necessary surface receptor for recognition by the bacterium.

Preferred target cells are eukaryotic cells. Even more preferred target cells are animal cells. "Animal cells" are defined as nucleated, non-chloroplast containing cells derived from or present in multicellular organisms whose taxanomic position lies within the kingdom animalia. The cells may be present in the intact animal, a primary cell culture, explant culture or a transformed cell line. The particular tissue source of the cells is not critical to the present invention.

The recipient animal cells employed in the present invention are not critical thereto and include cells present in or derived from all organisms within the kingdom animalia, such as those of the families mammalia, pisces, avian, reptilia.

Preferred animal cells are mammalian cells, such as humans, bovine, ovine, porcine, feline, canine, goat, equine, and primate cells. The most preferred animal cells are human cells.

In a preferred embodiment, the target cell is in a mucosal surface. Certain enteric pathogens, e.g., *E. coli*, Shigella, Listeria, and Salmonella, are naturally adapted for this application, as these organisms possess the ability to attach to and invade host mucosal surfaces (Kreig et al, supra). Therefore, in the present invention, such bacteria can deliver RNA molecules to cells in the host mucosal compartment.

Although certain types of bacteria may have a certain tropism, i.e., preferred target cells, delivery of RNA to a certain type of cell can be achieved by choosing a bacterium which has a tropism for the desired cell type or which is modified such as to be able to invade the desired cell type. Thus, e.g., a bacterium could be genetically engineered to mimic mucosal tissue tropism and invasive properties, as discussed above, to thereby allow said bacteria to invade mucosal tissue, and deliver RNA to cells in those sites.

Bacteria can also be targeted to other types of cells. For example, bacteria can be targeted to erythrocytes of humans and primates by modifying bacteria to express on their surface either, or both of, the *Plasmodium vivax* reticulocyte binding proteins-1 and -2, which bind specifically to erythrocytes in humans and primates (Galinski et al, *Cell*, 69:1213–1226 (1992)). In another embodiment, bacteria are modified to have on their surface asialoorosomucoid, which is a ligand for the asilogycoprotein receptor on hepatocytes (Wu et al, *J. Biol. Chem.*, 263:14621–14624 (1988)). In yet another embodiment, bacteria are coated with insulin-poly-L-lysine, which has been shown to target plasmid uptake to cells with an insulin receptor (Rosenkranz et al, *Expt. Cell Res.*, 199:323–329 (1992)). Also within the scope of the invention are bacteria modified to have on their surface p60 of *Listeria monocytogenes*, which allows for tropism for hepatocytes (Hess et al, *Infect. Immun.*, 63:2047–2053 (1995)), or a 60 kD surface protein from *Trypanosoma cruzi* which causes specific binding to the mammalian extracellular matrix by binding to heparin, heparin sulfate and collagen (Ortega-Barria et al, *Cell*, 67:411–421 (1991)).

In another embodiment, a bacterium is genetically engineered to express an antibody molecule, derivative thereof, or fragment thereof, on its surface, wherein the antibody is specific for a cell surface antigen of the desired target cell. In yet another embodiment, an antibody molecule, derivative thereof or fragment thereof is linked covalently or non-covalently to the surface of the bacteria, as set forth above.

Yet in another embodiment, a cell can be modified to become a target cell of a bacterium for delivery of RNA. Accordingly, a cell can be modified to express a surface antigen which is recognized by a bacterium for its entry into the cell, i.e., a receptor of an invasion factor. The cell can be modified either by introducing into the cell a nucleic acid encoding a receptor of an invasion factor, such that the surface antigen is expressed in the desired conditions. Alternatively, the cell can be coated with a receptor of an invasion factor. Receptors of invasion factors include proteins belonging to the integrin receptor superfamily. A list of the type of integrin receptors recognized by various bacteria and other microorganisms can be found, e.g., in Isberg and Tran Van Nhieu (1994) *Ann. Rev. Genet.* 27:395. Nucleotide sequences for the integrin subunits can be found, e.g., in GenBank, publically available on the internet.

As set forth above, yet other target cells include fish, avian, and reptilian cells. Examples of bacteria which are naturally invasive for fish, avian, and reptilian cells are set forth below.

Examples of bacteria which can naturally access the cytoplasm of fish cells include, but are not limited to *Aeromonas salminocida* (ATCC No. 33658) and *Aeromonas schuberii* (ATCC No. 43700). Attenuated bacteria are preferably used in the invention, and include *A. salmonicidia* vapA (Gustafson et al, *J. Mol. Biol.*, 237:452–463 (1994)) or *A. salmonicidia* aromatic-dependent mutant (Vaughan et al, *Infect. Immun.*, 61:2172–2181 (1993)).

Examples of bacteria which can naturally access the cytoplasm of avian cells include, but are not restricted to, *Salmonella galinarum* (ATCC No. 9184), *Salmonella ente-*

*riditis* (ATCC No. 4931) and *Salmonella typhimurium* (ATCC No. 6994). Attenuated bacteria are preferred to the invention and include attenuated Salmonella strains such as *S. galinarum* cya crp mutant (Curtiss et al, (1987) supra) or *S. enteritidis* aroA aromatic-dependent mutant CVL30 (Cooper et al, *Infect. Immun.*, 62:4739–4746 (1994)).

Examples of bacteria which can naturally access the cytoplasm of reptilian cells include, but are not restricted to, *Salmonella typhimurium* (ATCC No. 6994). Attenuated bacteria are preferable to the invention and include, attenuated strains such as *S. typhimuirum* aromatic-dependent mutant (Hormaeche et al, supra).

The invention also provides for delivery of RNA to other eukaryotic cells, e.g., plant cells, so long as there are microorganisms which are capable of invading such cells, either naturally or after having been modified to become invasive. Examples of microorganisms which can invade plant cells include *Agrobacterium tumerfacium*, which uses a pilus-like structure which binds to the plant cell via specific receptors, and then through a process that resembles bacterial conjugation, delivers at least some of its content to the plant cell.

Set forth below are examples of cell lines to which RNA can be delivered according to the method of this invention.

Examples of human cell lines include but are not limited to ATCC Nos. CCL 62, CCL 159, HTB 151, HTB 22, CCL 2, CRL 1634, CRL 8155, HTB 61, and HTB104.

Examples of bovine cell lines include ATCC Nos. CRL 6021, CRL 1733, CRL 6033, CRL 6023, CCL 44 and CRL 1390.

Examples of ovine cells lines include ATCC Nos. CRL 6540, CRL 6538, CRL 6548 and CRL 6546.

Examples of porcine cell lines include ATCC Nos. CL 184, CRL 6492, and CRL 1746.

Examples of feline cell lines include CRL 6077, CRL 6113, CRL 6140, CRL 6164, CCL 94, CCL 150, CRL 6075 and CRL 6123.

Examples of buffalo cell lines include CCL 40 and CRL 6072.

Examples of canine cells include ATCC Nos. CRL 6213, CCL 34, CRL 6202, CRL 6225, CRL 6215, CRL 6203 and CRL 6575.

Examples of goat derived cell lines include ATCC No. CCL 73 and ATCC No. CRL 6270.

Examples of horse derived cell lines include ATCC Nos. CCL 57 and CRL 6583.

Examples of deer cell lines include ATCC Nos. CRL 6193–6196.

Examples of primate derived cell lines include those from chimpanzee's such as ATCC Nos. CRL 6312, CRL 6304, and CRL 1868; monkey cell lines such as ATCC Nos. CRL 1576, CCL 26, and CCL 161; orangautan cell line ATCC No. CRL 1850; and gorilla cell line ATCC No. CRL 1854.

3. RNA That can be Delivered to a Target Cell 3.1 RNA That can be Translated in a Eukaryotic Cell The invention provides a method for delivering RNA to a eukaryotic cell, e.g., an animal cell. In a preferred embodiment, the RNA is capable of being translated in the eukaryotic cell.

As is well known in the art, translation of RNA into a protein in a eukaryotic cell requires RNA modifications and/or regulatory elements which differ from those required for translation of an RNA in a prokaryotic cell. RNA which is capable of being translated in a eukaryotic cell is referred to herein as "eukaryotic RNA". RNA which is capable of being translated in a prokaryotic cell is referred to herein as "prokaryotic RNA". In particular, prior to the initiation of translation of eukaryotic RNA, the 5' end of the RNA molecule is "capped" by addition of methylated guanylate to the first RNA nucleotide residue in the nucleus (Darnell et al, supra; Lewin, supra; Watson et al, supra; and Alberts et al, supra). Capping provides a recognition template for eukaryotic ribosomes and/or stabilizes the mRNA in the cytoplasm. Capping of RNA does not occur in prokaryotic cells and thus, normally, a prokaryotic RNA is not efficiently translated in a eukaryotic cell, e.g., animal cell. However, specific modifications to prokaryotic RNA can be effected to render the RNA translatable in eukaryotic cells. For example, it is possible for cap-independent translation initiation to occur by including a cap-independent translation enhancer (CITE) sequence, such as those derived from viruses, e.g., the cardioviruses including encephalomyocarditis virus (Duke et al, *J. Virol,* 66:1602–1609 (1992), U.S. Pat. No. 5,135,855 by Moss et al. and U.S. Pat. No. 4,937,190 by Palmenberg et al.), Mengovirus, Mous-Elberfeld virus, MM virus, and Columbia SK virus (U.S. Pat. No. 4,937,190 by Palmenberg et al.); Semliki Forest Virus (SFV); poliovirus (U.S. Pat. No. 5,358,856 by Baltimore et al., and, adenovirus. Such sequences are usually present in the 5' untranslated regions of these viruses. As used herein, "CITE sequences", also referred to herein as "Internal Ribosome Entry Site" and "IRES sequence", are any nucleotide sequences, which, when present in an RNA molecule, increase the translation efficiency of the RNA molecule in eukaryotic cells. Such sequences are preferably present downstream of a promoter, but upstream of the coding region of the RNA. Furthermore, it will be obvious to those skilled in the art that it is possible to express multiple products from a single mRNA molecule (i.e., polycistronic RNA) by inserting a CITE sequence upstream of each coding region of the RNA. CITE sequences are further described in the following references: Borman, A. M. et al. (1997) *Nucleic Acids Research* 25:925; Rijnbrand, R. et al. (1997) *Journal of Virology* 71:451; Shiroki, K. et al. (1997) *Journal of Virology* 71:1; Agol, V. I. et al. (1996) *Journal of Biotechnology* 44:119; Das, S. et al. (1996) *Journal of Virology* 70:1624; Barton, D. J. et al. (1996) *Virology* 217:459; Schultz, D. E. et al. (1996) *Journal of Virology* 70:1041; Aldabe, R. et al. (1995) *FEBS Letters* 377; Degener, A. M. et al. (1995) *Virus Research* 37:291; Ziegler, E. et al. (1995) *Virology* 213:549; Vagner, S. et al. (1995) *Journal of Biological Chemistry* 270:20376; Sjoberg, E. M. et al. (1994) *Bio/Technology* 12:1127; Yoo, B. J. et al. (1992) *Virology* 191:889; Donze, O. and P. F. Spahr. (1992) *EMBO Journal* 11:3747; Kwee, L. et al. (1992) *Journal of Virology* 66:4382; Forman, B. M. and H. H. Samuels. (1991) *Gene* 105:9; Ruiz-Linares, A. et al. (1989) *Nucleic Acids Research* 17:2463; Wang et al (1997) EMBO J. 16:4 107; Gan et al (1996) *J. Biol. Chem.* 271:623; Turner et al (1976) Arch. Virol. 134:321; Danthinne et al. (1993) *Mol. Cell. Biol.* 13:3340; Duke et al (1992) *J. Virol.* 66:1602; Davies et al (1991) *J. Biol. Chem.* 266:14714; Dolph et al; (1990) *J. Virol.* 64:2669; Ratner (1989) *Nucl. Acids Res.* 12:4101.

CITE sequences can be linked to an RNA, e.g., by transcription of an RNA from a promoter located upstream of a CITE sequence, which in turn is located upstream of the coding region. CITE sequences strongly increase translation of RNA both in whole cells and in vitro translation systems, e.g., in a reticulocyte lysate (Elroy-Stein et al. (1989) *Proc. Natl. Acad. Sci. USA* 86:6126). A CITE sequence can have, e.g., the nucleotide sequence shown in FIG. 1 and set forth in SEQ ID NO. 1, which corresponds to the nucleotide sequence from nucleotide 2416 to nucleotide 2914 of pCITE-1 from Novagen, Inc. (Madison, Wis.). DNA vectors containing a CITE sequence cloned upstream of a polylinker, which were designed for transcription of RNA that can be translated in eukaryotic cells, are commercially available, and can be obtained, e.g., from Novagen, Inc. (Madison, Wis.) (pCITE vectors, which are further described in the Examples). Such vectors can be used for preparing nucleic acids of the invention, i.e., nucleic acids which can be transcribed into RNA in prokaryotic cells and wherein the RNA can subsequently be translated in eukaryotic cells.

The term "eukaryotic RNA expression cassette" is used herein to define a nucleic acid which comprises elements or sequences which, when present in an RNA molecule, significantly increase its translation efficiency in a eukaryotic cell. For example, a CITE sequence is a preferred element of a eukaryotic RNA expression cassette. Another sequence which may be included in a eukaryotic RNA expression cassette is a polyadenylate sequence. The presence of a polyadenylate tail on an RNA may improve its stability both in the invasive bacterium and in the target eukaryotic cells, and may therefore be a desirable element.

In contrast to a "eukaryotic RNA expression cassette", a "prokaryotic RNA expression cassette" refers to a nucleic acid which comprises elements or sequences which, when present in an RNA molecule, significantly increase its translation efficiency in a prokaryotic cell. Such elements are further described herein. As a point of comparison, a "DNA expression cassette" refers to a nucleic acid which comprises elements or sequences which, when present in a DNA molecule, significantly increases its transcription efficiency in a cell. Thus, if the elements increase the transcription efficiency in a eukaryotic cell (e.g., the element is a eukaryotic promoter), the cassette is a "eukaryotic DNA expression cassette", whereas, if the elements increase the transcription efficiency in a prokaryotic cell (e.g., the element is a prokaryotic promoter), the cassette is a "prokaryotic DNA expression cassette".

The eukaryotic RNA expression cassette may also contain specific sequences which stabilize the RNA, which destabilize the RNA, which increases its translation efficiency or which decreases its translation efficiency. For example, RNA destabilizing sequences, i.e., nucleotide sequences which when present in an RNA decreases the half-life of the RNA, can be AU-rich sequences, which are found, e.g., in the RNA encoding cytokines, e.g., lymphokines, such as interferon-beta and proto-oncogenes (Shaw and Kamen (1986) Cell 46:659). Alternatively, if one desires to express cytokines or products of genes having such destabilizing elements, it may be desirable to remove or destroy such destabilizing sequences, e.g., by mutagenesis.

In a preferred embodiment, the RNA contains upstream of the CITE sequence a nucleotide sequence which can prevent degradation of a CITE sequence by a 5'-3' exonuclease activity. While no such RNAse activity has been identified in enteric bacteria (reviewed in Kushner. "mRNA Decay" in Neidhhart et al. Eds. Escherichia coli and Salmonella. Cellular and Molecular Biology. Second ed. Vol. 1. Washington D.C.: ASM Press, 1996:849), it may be desirable in certain situations to add a 5' nucleotide sequence which would significantly reduce degradation of the CITE sequence. A preferred nucleotide sequence that can be inserted upstream of the CITE sequence is at least a portion of a 5' untranlated region of OmpA, which forms a three stem-loop structure and has been shown to impart stability to RNA (Emory et al. (1992) Genes Dev. 6:135).

In another embodiment of the invention, the level of translation of a specific RNA is increased by modifying the RNA to include nucleotide sequences which improve the translation efficiency of an RNA. Such sequences can be located, e.g., in the 5' untranslated region of a mRNA. For example, the ferritin mRNA comprises an iron regulatory element (IRE) in the 5' untranslated (UT) region of its mRNA, which increases translation of the mRNA in the presence of iron. In conditions of iron deprivation, a binding protein, IRE-BP, specifically interacts with the IRE sequence and represses translation (Kuhn et al. (1993) J. Inorg. Biochem. 47:183).

Thus, based at least on the possible presence of specific elements in, 5' or 3' untranslated regions of RNAs which influence stability and/or translation efficiency, constitutively, or in an inducible manner, the stability and/or translation efficiency of specific RNAs will vary depending on whether 5' and/or 3' untranslated regions are present. The effect of the presence of 5' and/or 3' untranslated regions or portions thereof in an RNA can be determined experimentally, e.g., by transfection experiments. For example, RNA stability may be determined by pulse labeling experiments. Accordingly, the invention provides methods for delivering RNA to eukaryotic cells, wherein the amount of protein synthesized in the eukaryotic cell from the RNA can be controlled by modifying the RNA such as to effect its translation efficiency and/or half-life.

The eukaryotic RNA expression cassette can also encode self-amplifying sequences. For example, the RNA expression cassette can encode an attenuated alpha virus, such as Venezuela equine encephalitis virus (VEE), semiliki forest virus (SFV), or sindbis virus, that have been modified to express passenger vaccine antigens (Pushko P et al., 1997 Virology 239:389–401; Tsuji M et al., 1998, J. Virol. 72:6907–10; Hariharan M. J., et al., 1998 J. Virol., 72:950–8; Gorrell M. D., et. al., 1997, J. Virol. 71:3415–9). Self-amplifying RNA expression cassettes can be expressed in eukaryotic cells by delivering to the eukaryotic cells RNA molecules that were transcribed in the bacterial vector and subsequently amplified in the target eukaryotic cells. An example of a self-amplifying RNA expression cassette is set forth in FIG. 2. In this example, the RNA sequence is translated by the host cell following recognition of IRES-1 (Duke et al. (1992) J. Virol 66(3): 1602–9) at the 5-prime end of the RNA molecule (FIG. 2), thereby resulting in the synthesis of the alphavirus replicase (Pushko et al. (1997) Virology 239(2): 389–401). The replicase then binds to the IRES-2 sequence (Pushko et al. (1997) Virology 239(2): 389–401) and produces as many as $10^5$ positive mRNA copies, that are subsequently translated by the host cell ((Pushko et al. (1997) Virology 239(2): 389–401); see also FIG. 2).

Figure 3:
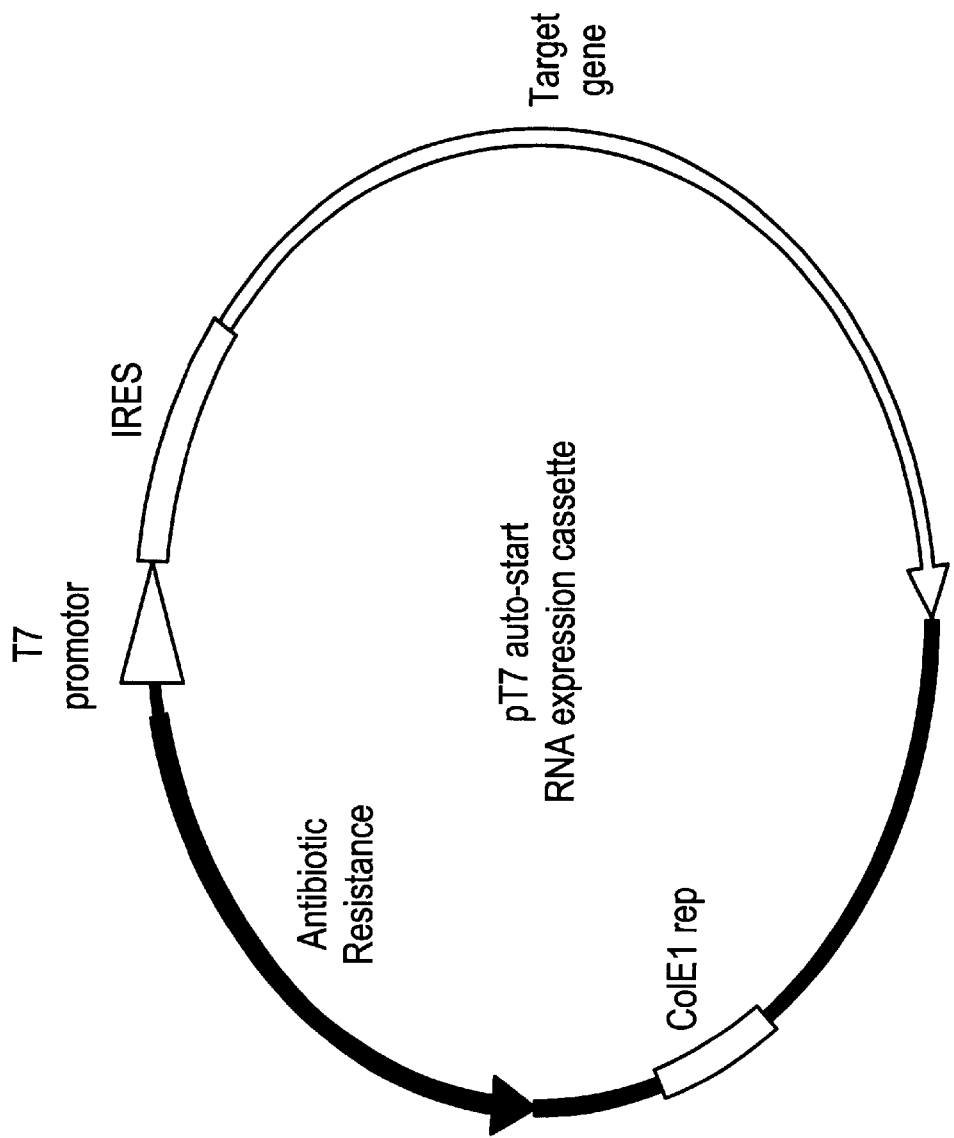
FIG. 3 is a diagram of a generic plasmid design of a cytoplasmic-launch Env RNA vector.
Figure 4:
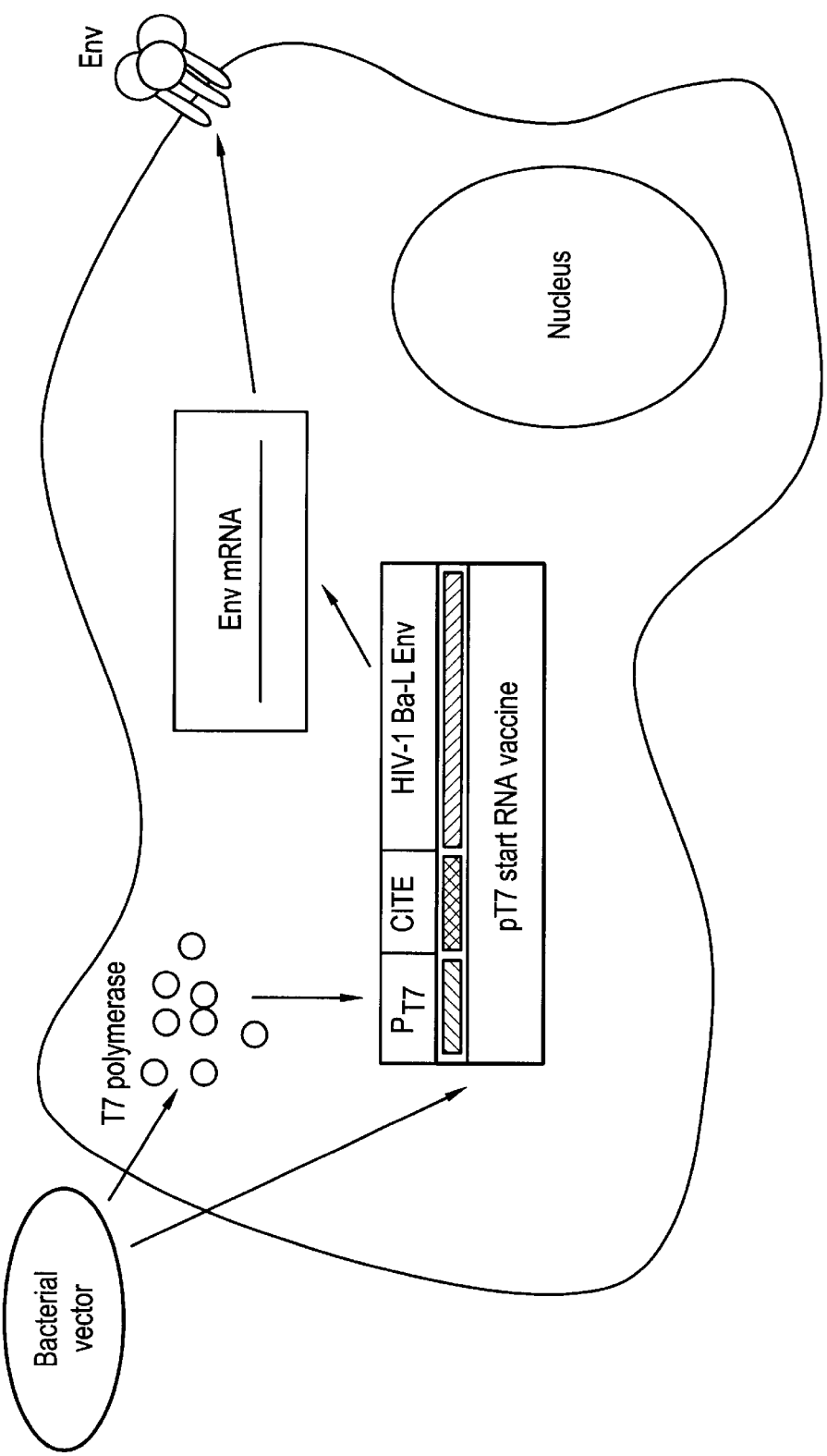
FIG. 4 is a diagram of the cytoplasmic expression of Env from a cytoplasmic-launch Env RNA vector.

Alternatively, RNA expression cassettes can be transcribed directly in the eukaryotic cell by including a T7 promoter upstream of the RNA expression cassette and simultaneously delivering T7 polymerase to the eukaryotic cell (See FIGS. 3 and 4) (Selby M. J., 1997, J. Virol. 71:7827–31). Alternatively, expression of the self-amplifying RNA expression cassette can be initiated by including a eukaryotic promoter (Hariharan M. J., et al., 1998 J. Virol., 72:950–8).

In another embodiment, the invention provides a bacterium comprising a nucleic acid which is capable of being transcribed into RNA in the bacterium, wherein the RNA is capable of being translated in a eukaryotic cell as well as in the bacterium. Accordingly, in one embodiment of the invention, the RNA comprises regulatory sequences necessary for translation of the RNA in eukaryotic cells, e.g., a CITE sequence, as well as regulatory elements necessary for translation of the RNA in prokaryotic cells, e.g., a Shine- Dalgarno ribosome binding site. The necessary elements for efficient translation in a prokaryotic cell are referred to herein as "prokaryotic expression cassette". Thus, in one embodiment, a desired gene product can be synthesized both in the bacterium and the eukaryotic target cell. Such an embodiment can be of interest if the desired gene product, i.e., protein, is not heavily posttranslationally modified, when the posttranslational modifications are not required to achieve the desired effects, or when such combinations are found to improve the immunogenicity of a product that is intended to be a vaccine antigen.

The RNA may allow expression of either a foreign or an endogenous protein. As used herein, "foreign protein" or "heterologous protein" refers to a protein, which is foreign to the recipient eukaryotic cell or tissue, such as a vaccine antigen, immunoregulatory agent, or therapeutic agent. An "endogenous protein" refers to a protein which is naturally present in the recipient animal cell or tissue.

The RNA or DNA wich is translated into RNA in a bacterium is preferably heterologous with respect to the bacterium or with respect to the bacterial nucleic acids, i.e., not naturally present in the bacterium or nucleic acids. The RNA or DNA of the invention can also be "non-prokaryotic" (i.e., naturally present only in non-prokaryotic nucleic acids); "non-bacterial" (i.e., naturally present only in non-bacterial nucleic acids); "non-viral" (i.e., naturally present only in non-viral nucleic acids; "non-eukaryotic" (i.e., naturally present only in non-eukaryotic nucleic acids).

In addition, in most embodiments of the invention, the polypeptide encoded by the RNA will not be a polypeptide that is typically encoded by a bacterial plasmid, such as for providing resistance to a specific drug. Similarly, whereas in certain embodiments, the polypeptide is a polypeptide which has as its sole utility to serve as a marker, e.g., to track the cells expressing the polypeptide, in preferred embodiments, the RNA delivered by the bacteria will not encode a "marker polypeptide" or "reporter polypeptide", such as beta-galactosidase. In cases in which DNA encoding a marker or reporter polypeptide is used in the invention, it is preferably used together with DNA encoding a non-marker or non-reporter polypeptide or an antisense RNA or a ribozyme RNA.

In a preferred embodiment, the RNA delivered to the eukaryotic cell which is translated in the eukaryotic cell is a vaccine antigen. As used herein, a "vaccine antigen" refers to a polypeptide or derivative thereof, which can be used to vaccinate a subject, i.e., to mount an immune response in the subject against the antigen. A vaccine antigen may be a protein or antigenic fragment thereof from viral pathogens, bacterial pathogens, and parasitic pathogens. Alternatively, the vaccine antigen may be a synthetic polypeptide, constructed using recombinant DNA methods, which contains antigens or parts thereof from viral, bacterial, parasitic pathogens. These pathogens can be infectious in humans, domestic animals or wild animals. In addition, multiple RNA molecules can be delivered that express any combination of viral, bacterial, parasitic antigens, or said synthetic antigens. The antigen or synthetic antigen can be any molecule or part thereof that is expressed by any viral, bacterial, or parasitic pathogen prior to or during entry into, colonization of, or replication of, their animal host.

Preferred viral pathogens, from which the viral antigens are derived, include, but are not limited to, Orthomyxoviruses, such as influenza virus; Retroviruses, such as Human T Lymphotrophic Virus (HTLVI, e.g., HTLV-1, HTLV-2, and HTLV-5), Human Immunodeficiency Virus (HIV, e.g., HIV-1, HIV-2), and SIV; Herpesviruses, such as Epstein-Barr Virus (EBV), Cytomegalo virus (CMV) or Herpes Simplex Virus (HSV); Rhabdoviruses, such as rabies virus; Picornoviruses, such as poliovirus; Poxviruses, such as vaccinia; Rotavirus; and Parvoviruses.

Examples of vaccine antigens of viral pathogens include, but are not limited to, the human immunodeficiency virus antigens Nef, Gag, Env, gp120, gp41, Tat, Rev, and Pol (Hahn et al, *Nature,* 313:277–280 (1985)) and T cell and B cell epitopes of gp120 (Palker et al, *J. Immunol.,* 142:3612–3619 (1989)); the hepatitis B surface antigen (Wu et al, *Proc. Natl. Acad. Sci., USA,* 86:4726–4730 (1989)); rotavirus antigens, such as VP4 (Mackow et al, *Proc. Natl. Acad. Sci., USA,* 87:518–522 (1990)) and VP7 (Green et al, *J. Virol.,* 62:1819–1823 (1988)), influenza virus antigens such as hemagglutinin or nucleoprotein (Robinson et al., Supra; Webster et al, Supra) and herpes simplex virus thymidine kinase (Whitley et al, In: *New Generation Vaccines,* pages 825–854).

Bacterial pathogens, from which the bacterial antigens can be derived, include but are not limited to, Mycobacterium spp., *Helicobacter pylori,* Salmonella spp., Shigella spp., *E. coli,* Rickettsia spp., Listeria spp., *Legionella pneumoniae,* Pseudomonas spp., Vibrio spp., and *Borellia burgdorferi.*

Examples of vaccine antigens of bacterial pathogens include CFA/I fimbrial antigen of enterotoxigenic *E. coli* (Yamamoto et al, *Infect. Immun.,* 50:925–928 (1985)), cholera toxin of *Vibrio cholerae* (Mekalanos et al (1992) PNASUSA 79:151), heat-labile enterotoxin of *Escherichia coli* (L T; Moseley, L. L. et al. (1983) Infection & Immunity 39:1167; Moseley, L. L. et al. (1983) Journal of Bacteriology 156:441), and the nontoxic B-subunit of CT and LT (Clements et al, 46:564–569 (1984)); pertactin of *Bordetella pertussis* (Roberts et al, *Vacc.,* 10:43–48 (1992)), adenylate cyclase-hemolysin of *B. pertussis* (Guiso et al, *Micro. Path.,* 11:423–431 (1991)), and fragment C of tetanus toxin of *Clostridium tetani* (Fairweather et al, *Infect. Immun.,* 58:1323–1326 (1990)).

Parasitic pathogens, from which the parasitic antigens can be derived, include but are not limited to, Plasmodium spp., Trypanosome spp., Giardia spp., Boophilus spp., Babesia spp., Entamoeba spp., Eimeria spp., Leishmania spp., Schistosome spp., Brugia spp., Fascida spp., Dirofilaria spp., Wuchereria spp., and Onchocerea spp.

Examples of vaccine antigens of parasitic pathogens include the circumsporozoite antigens of Plasmodium spp. (Sadoff et al, *Science,* 240:336–337 (1988)), such as the circumsporozoite antigen of *P. falciparum;* the merozoite surface antigen of Plasmodium spp. (Spetzler et al, *Int. J. Pept. Prot. Res.,* 43:351–358 (1994)); the galactose specific lectin of *Entamoeba histolytica* (Mann et al, *Proc. Natl. Acad. Sci., USA,* 88:3248–3252 (1991)), gp63 of Leishmania spp. (Russell et al, *J. Immunol.,* 140:1274–1278 (1988)), paramyosin of *Brugia malayi* (Li et al, *Mol. Biochem. Parasitol.,* 49:315–323 (1991)), the triose-phosphate isomerase of *Schistosoma mansoni* (Shoemaker et al, *Proc. Natl. Acad. Sci., USA,* 89:1842–1846 (1992)); the secreted globin-like protein of *Trichostrongylus colubriformis* (Frenkel et al, *Mol. Biochem. Parasitol.,* 50:27–36 (1992)); the glutathione-S-transferase of *Frasciola hepatica* (Hillyer et al, *Exp. Parasitol,* 75:176–186 (1992)), *Schistosoma bovis* and *S. japonicum* (Bashir et al, *Trop. Geog. Med.,* 46:255–258 (1994)); and KLH of *Schistosoma bovis* and *S. japonicum* (Bashir et al, supra).

In the present invention, bacteria can also deliver RNA molecules encoding a therapeutic vaccine. As used herein, "therapeutic vaccine" refers to a vaccine comprising a therapeutic agent, which is a eukaryotic protein or peptide which is present or may be present in a subject, the shielding of which or elimination of which is desired. For example, the RNA molecules can encode a tumor-specific, transplant, or autoimmune antigen or part thereof.

Examples of tumor vaccine antigens include prostate specific antigen (Gattuso et al, *Human Pathol.,* 26:123–126 (1995)), TAG-72 and carcinoembryonic antigen (CEA) (Guadagni et al, *Int. J. Biol. Markers,* 2:53–60 (1994)), MAGE-1 and tyrosinase (Coulie et al, *J. Immunothera.,* 14:104–109 (1993)). Yet any other tumor antigen can also be used according to the method of the invention, to elicit an immune reaction against tumor cells expressing the antigen. It has in fact been shown in mice that immunization with non-malignant cells expressing a tumor antigen provides a vaccine effect, and also helps the animal mount an immune response to clear malignant tumor cells displaying the same antigen (Koeppen et al, *Anal. N.Y. Acad. Sci.,* 690:244–255 (1993)). Accordingly, tumor specific antigens can be delivered to a subject having a tumor or likely to develop a tumor according to the method of the invention to thereby induce an immune reaction against the tumor and either reduce or elimate the tumor or prevent a tumor from developing.

Examples of transplant antigens that can be administered to a subject according to the method of the invention include the CD3 receptor on T cells (Alegre et al, *Digest. Dis. Sci.,* 40:58–64 (1995)). In fact, it has been shown that treatment with an antibody to CD3 receptor results in rapid clearance of circulating T cells and reverses most rejection episodes (Alegre et al, supra). The invention provides for administration of any transplant antigen. As used herein, the term "transplant antigen" refers to an antigen which is involved in an immune reaction and includes antigens involved in transplant rejections and antigens involved in establishment of tolerance. Accordingly, transplant antigens include antigens involved in the interaction of B and T cells with other cells, e.g., antigen presenting cells. Transplant antigens within the scope of the invention include costimulatory molecules or receptors thereof, e.g., B7-1, B7-2, CD28, CTLA4; gp39 (also termed CD40 ligand); CD40; CD4; CD8; major histocompatibility complex antigens (MHC), e.g., MHC class I and MHC class II; and adhesion factors, e.g., LFA-1, LFA-3, ICAM-1, VLA4, and CD2. Without wanting to be limited to a specific mechanism of action, administration of a transplant antigen to a subject according to the method of the invention results in stimulation a humoral and/or cell-mediated immune response against the antigen, thereby resulting in inhibiting or at least reducing the interaction of the transplant antigen with its receptor or destroying the cells carrying the antigen, thereby establishing tolerance.

The method of the invention can also be used to destroy autoimmune cells. According to the method of the invention, an autoimmune antigen is administered to a subject prophylactically or therapeutically, to thereby result in the production of antibodies against the autoimmune antigen, thereby inducing destruction of autoimmune cells or preventing their development. Examples of autoimmune antigens include IAS β chain (Topham et al, *Proc. Natl. Acad. Sci., USA,* 91:8005–8009 (1994)). In fact, it has been shown that vaccination of mice with an 18 amino acid peptide from IAS β chain provides protection and treatment to mice with experimental autoimmune encephalomyelitis (Topham et al, supra).

Alternatively, in the present invention, bacteria can deliver RNA molecules encoding immunoregulatory molecules, e.g., to boost the immune response against said antigens. These immunoregulatory molecules include, but are not limited to, growth factors, such as M-CSF, GM-CSF, erythropoietin; and cytokines, such as IL-2, IL-4, IL-5, IL-6, IL-10, IL-12 or IFN-γ, clotting factors, tissue plasminogen activators, recombinant soluble receptors, e.g., IL-1 or TNF receptor. Furthermore, delivery of cytokines expression cassettes to tumorous tissue has been shown to stimulate potent systemic immunity and enhanced tumor antigen presentation without systemic cytokine toxicity (Golumbek et al, *Canc. Res.,* 53:5841–5844 (1993); Golumbek et al, *Immun. Res.,* 12:183–192 (1993); Pardoll, *Curr. Opin. Oncol.,* 4:1124–1129 (1992); and Pardoll, *Curr. Opin. Immunol.,* 4:619–623 (1992)).

Yet other proteins or polypeptides can be delivered to eukaryotic cells according to the method of the invention. Generally, any peptide that is beneficial to a subject can be administered. Thus, the invention can be used in gene therapy in general. For example, the peptide can be a peptide which is deficient in a subject and the method of the invention provides a method for compensating for the deficient peptide. The peptide can be secreted, membraneous, or cytoplasmic.

3.2 Antisense RNAs and Catalytic RNAs

In another embodiment, the invention relates to the delivery of RNA in "antisense" therapy. As used herein, "antisense" therapy refers to administration or in situ generation of nucleic acid molecules, e.g., RNA, or their derivatives which specifically hybridize (e.g., bind) under cellular conditions, with the cellular RNA, e.g., mRNA, and/or genomic DNA, so as to, e .g., inhibit expression of a specific protein, e.g. by inhibiting transcription and/or translation. The binding may be by conventional base pair complementarity, or, for example, in the case of binding to DNA duplexes, through specific interactions in the major groove of the double helix. Absolute complementarity between the antisense RNA molecule and the target molecule, although preferred, is not required. An RNA sequence "complementary" to a portion of a nucleic acid, as referred to herein, means a sequence having sufficient complementarity to be able to hybridize with the nucleic acid, forming a stable duplex or triplex. The ability to hybridize will depend on both the degree of complementarity and the length of the antisense RNA. Generally, the longer the hybridizing RNA, the more base mismatches with an RNA it may contain and still form a stable duplex (or triplex, as the case may be). One skilled in the art can ascertain a tolerable degree of mismatch by use of standard procedures to determine the melting point of the hybridized complex.

Antisense RNAs which are complementary to the 5' end of an RNA message, e.g., the 5' untranslated sequence up to and including the AUG initiation codon, should work most efficiently at inhibiting translation. However, sequences complementary to the 3' untranslated sequences of mRNAs have also been shown to be effective at inhibiting translation of mRNAs as well. (Wagner, R. (1994) *Nature* 372:333). Therefore, antisense RNAs complementary to either the 5' or 3' untranslated, non-coding regions of a gene could be used in an antisense approach to inhibit translation of endogenous mRNA. Antisense RNAs complementary to the 5' untranslated region of the mRNA should include the complement of the AUG start codon. Antisense RNAs complementary to mRNA coding regions may be less efficient inhibitors of translation but could be used in accordance with the invention. Whether designed to hybridize to the 5', 3' non coding or coding region of a mRNA, antisense RNAs should be at least six nucleotides in length, and are preferably ranging from 6 to about 50 nucleotides in length. In certain embodiments, the RNA is at least 50 nucleotides, at least 70 nucleotides, at least 90 nucleotides, or at least 100 nucleotides.

Regardless of the choice of target sequence, it is preferred that in vitro studies are first performed to quantitate the ability of the antisense RNA to inhibit gene expression. It is preferred that these studies utilize controls that distinguish between antisense gene inhibition and nonspecific biological effects of antisense RNAs. It is also preferred that these studies compare levels of the target RNA or protein with that of an internal control RNA or protein. Additionally, it is envisioned that results obtained using the antisense RNA are compared with those obtained using a control RNA, e.g., a sense RNA. It is preferred that the control RNA is of approximately the same length as the test RNA and that the nucleotide sequence of the antisense RNA differs from the antisense sequence no more than is necessary to prevent specific hybridization to the target sequence.

In addition to the sequence complementary to a target sequence, the antisense RNA can comprise sequences which are capable of modulating the stability of the RNA. Accordingly, the same sequences set forth above for either enhancing or decreasing RNA stability, e.g., AU-rich sequences, can be linked to the antisense sequence per se. Alternatively, the portion of the antisense RNA which is complementary to the target sequence can be modified to eliminate specific sequences, e.g., sequences rendering the RNA unstable, so long as the antisense RNA is still capable of hybridizing to the target sequence. Modification of the antisense RNA can be performed according to methods known in the art, e.g., site directed mutagenesis.

The invention also provides a method for delivering catalytic RNAs to a eukaryotic cell. In a preferred embodiment, the catalytic RNA is a ribozyme. Ribozyme molecules designed to catalytically cleave specific mRNA transcripts can be used to prevent translation of mRNA and expression of specific proteins in eukaryotic cells. (See, e g., PCT International Publication WO 94/11364, published Oct. 4, 1990; Sarver et al., 1990, Science 247:1222–1225). Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the RNA sequence unsuitable. The suitability of candidate sequences may also be evaluated by testing their accessibility to hybridization with complementary oligonucleotides, using ribonuclease protection assays.

While ribozymes that cleave mRNA at site specific recognition sequences can be used to destroy specific mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are usually hundreds of potential hammerhead ribozyme cleavage sites within the nucleotide sequence of a specific mRNA. Preferably the ribozyme is engineered so that the cleavage recognition site is located near the 5' end of the mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al. (1984) Science 224:574–578; Zaug and Cech (1986) Science 231:470–475; Zaug, et al. (1986) Nature 324:429–433; published International patent application No. WO88/04300 by University Patents Inc.; Been and Cech (1986) Cell 47:207–216). The Cech-type ribozymes have an eight base pair active site which hybridizes to a target RNA sequence whereafter cleavage of the target RNA takes place.

As in the antisense approach, the ribozymes can be composed of modified RNAs (e.g., for improved stability). Because ribozymes, unlike antisense molecules, are catalytic, a lower intracellular concentration is required for efficiency.

The antisense RNA and catalytic RNA species delivered to animal cells can be targeted against any molecule present within the recipient cell or likely to be present within the recipient cell. These include but are not limited to RNA species encoding cell regulatory molecules, such as interlukin-6 (Mahieu et al, Blood, 84:3758–3765 (1994)), oncogenes such as ras (Kashani-Sabet et al, Antisen. Res. Devel., 2:3–15 (1992)), causative agents of cancer such as human papillomavirus (Steele et al, Canc. Res., 52:4706–4711 (1992)), enzymes, viral RNA's and pathogen derived RNA's such as HIV-1 (Meyer et al, Gene, 129:263–268 (1993); Chatterjee et al, Sci., 258:1485–1488 (1992); and Yamada et al, Virol, 205:121–126 (1994)). The RNAs can also be targeted at non-transcribed DNA sequences, such as promoter or enhancer regions, to form, e.g., triplex molecules, or to any other molecule present in the recipient cells, such as but not limited to, enzymes involved in DNA synthesis or tRNA molecules (Scanlon et al, Proc. Natl. Acad. Sci. USA, 88:10591–10595 (1991); and Baier et al, Mol. Immunol., 31:923–932 (1994)).

As a further alternative, single or multiple RNA molecules encoding a vaccine antigen, a therapeutic antigen, or which are antisense or catalytic RNA can be delivered in any combination.

4. Introduction of RNA into a Bacterium for Delivery to a Eukaryotic Cell

In a preferred embodiment of the invention, the RNA is synthesized in the bacterium, and the RNA is delivered to the eukaryotic cell upon invasion of the eukaryotic cell by the bacterium.

In one embodiment, the RNA which is capable of being translated in a eukaryotic cell or which is an antisense or a catalytic RNA is encoded by DNA that is operably linked to a bacterial promoter, e.g., the anaerobic E. coli, NirB promoter or the E. coli lipoprotein llp promoter, described, e.g., in Inouye et al. (1985) Nucl. Acids Res. 13:3101; Salmonella pagC promoter (Miller et al., supra), Shigella ent promoter (Schmitt and Payne, J. Bacteriol. 173:816 (1991)), the tet promoter on Tn10 (Miller et al., supra), or the ctx promoter of *Vibrio cholera*. Any other promoter can be used in the invention. The bacterial promoter can be a constitutive promoter or an inducible promoter. A preferred inducible promoter is a promoter which is inducible by iron or in iron-limiting conditions. In fact, some bacteria, e.g., intracellular organisms, are believed to encounter iron-limiting conditions in the host cytoplasm. Examples of iron-regulated promoters of FepA and TonB. are known in the art and are described, e.g., in the following references: Headley, V. et al. (1997) *Infection & Immunity* 65:818; Ochsner, U. A. et al. (1995) *Journal of Bacteriology* 177:7194; Hunt, M. D. et al. (1994) *Journal of Bacteriology* 176:3944; Svinarich, D. M. and S. Palchaudhuri. (1992) *Journal of Diarrhoeal Diseases Research* 10:139; Prince, R. W. et al. (1991) *Molecular Microbiology* 5:2823; Goldberg, M. B. et al. (1990) *Journal of Bacteriology* 172:6863; de Lorenzo, V. et al. (1987) *Journal of Bacteriology* 169:2624; and Hantke, K. (1981) *Molecular & General Genetics* 182:288.

The nucleic acid to be transcribed and the promoter to which it is operably linked are preferably in a vector or plasmid. As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids contained therein. Vectors capable of directing the expression of genes to which they are operatively linked are referred to herein as "expression vectors". The term "plasmid" as used herein, refers generally to circular double stranded DNA loops which are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

A plasmid for practicing the invention preferably comprises sequences required for appropriate transcription of the nucleic acid in bacteria, e.g., a transcription termination signal. The vector can further comprise sequences encoding factors allowing for the selection of bacteria comprising the nucleic acid of interest, e.g., gene encoding a protein providing resistance to an antibiotic, sequences required for the amplification of the nucleic acid, e.g., a bacterial origin of replication.

In a preferred embodiment, the DNA is operably linked to a first promoter and the bacterium further comprises a second DNA encoding a first polymerase which is capable of mediating transcription from the first promoter, wherein the DNA encoding the first polymerase is operably linked to a second promoter. In a preferred embodiment, the second promoter is a bacterial promoter, such as those delineated above. In an even more preferred embodiment, the polymerase is a bacteriophage polymerase, e.g., SP6, T3, or T7 polymerase and the first promoter is a bacteriophage promoter, e.g., an SP6, T3, or T7 promoter, respectively. Plasmids comprising bacteriophage promoters and plasmids encoding bacteriophage polymerases can be obtained commercially, e.g., from Promega Corp. and InVitrogen, or can be obtained directly from the bacteriophage using standard recombinant DNA techniques (J. Sambrook, E. Fritsch, T. Maniatis, Molecular Cloning: A Laboratory Manual, Cold Spring Laboratory Press, 1989). Bacteriophage polymerases and promoters are further described, e.g., in the following references: Sagawa, H. et al. (1996) *Gene* 168:37; Cheng, X. et al. (1994) *PNAS USA* 91:4034; Dubendorff, J. W. and F. W. Studier (1991) *Journal of Molecular Biology* 219:45; Bujarski, J. J. and P. Kaesberg (1987) *Nucleic Acids Research* 15:1337; and Studier, F. W. et al. (1990) *Methods in Enzymology* 185:60). Such plasmids can further be modified according to the specific embodiment of the invention.

In another preferred embodiment, the bacterium further comprises a DNA encoding a second polymerase which is capable of mediating transcription from the second promoter, wherein the DNA encoding the second polymerase is operably linked to a third promoter. In a preferred embodiment, the third promoter is a bacterial promoter. However, more than two different polymerases and promoters could be introduced in a bacterium to obtain high levels of transcription. The use of one or more polymerase for mediating transcription in the bacterium can provide a significant increase in the production of RNA in the bacterium relative to a bacterium in which the DNA is directly under the control of a bacterial promoter. The selection of the system to adopt will vary depending on the specific use of the invention, e.g., on the amount of RNA that one desires to produce.

In certain embodiments, the DNA will allow transcription in the bacteria at least about 10 times, at least about 100 times, at least about 1,000 times or preferably at least about 10,000 times more efficiently than in eukaryotic cells. Thus, in preferred embodiments, the DNA is transcribed essentially only in prokaryotic cells. To achieve such prokaryotic specific transcription, the DNA containing the RNA expression cassette will contain promoters that are essentially only functional in prokaryotic cells, e.g., the lac promoter, the trc promoter, the lambda Pr, the T7 promoter, all of which are further described herein, and be devoid of any eukaryotic transcriptional promoters. Methods for proving that transcription is more efficient, or occurs essentially only, in prokaryotic cells relative to eukaryotic cells are described herein and are also known in the art. For example, the DNA of interest can be delivered to eukaryotic cells, e.g., by transfection, and the level of its expression determined. By comparison with appropriate controls, the absence of expression of the DNA in the eukaryotic cells indicates that transcription from this DNA does essentially not occur in eukaryotic cells.

In other embodiments, the DNA will allow transcription in bacteria and in eukaryotic cells. In these embodiments, the DNA will contain trancriptional regulatory elements directing transcription in prokaryotic cells and in eukaryotic cells. The same transcriptional element could direct transcription in these two types of cells, or alternatively, different transcriptional elements can direct transcription in each of these types of cells.

In other embodiments, it may be preferred to reduce to a minimum the amount of translation occurring in the bacteria, such that most of, or essentially all of, the RNA molecules in the bacteria are delivered to the eukaryotic cell and translated therein. Thus, in a preferred embodiment, the RNA is translated at least about 10 times, more preferably at least about 100 times, at least about 1,000 times, or even more preferably, at least about 10,000 times more efficiently in eukaryotic cells than in prokaryotic cells. Accordingly, in a preferred embodiment, the RNA is translated essentially only in eukaryotic cells. This can be achieved by choosing appropriate translational control elements, and can be tested according to methods described herein and methods known in the art. In particular, translation in prokaryotic cells can be avoided by excluding prokaryotic ribosome binding sites, which are characterized by the motif "AGGA (SEQ ID NO: 2)."

Generally, since prokaryotic and eukaryotic transcriptional and translational regulatory elements are well known in the art, one can design vectors that would allow transcription and translation selectively in prokaryotic and eukaryotic cells or, alternatively, in prokaryotic and eukaryotic cells. After designing a vector, it may be desirable to compare the nucleotide sequence of the vector with one or more sequence database of regulatory control elements, to determine if a cryptic regulatory element, e.g., one that was introduced as a result of the ligation of different fragments of DNA together, is present. A homology with a know regulatory element, e.g., eukaryotic promoter, may indicate that some transcription in eukaryotic cells may occur. If such a cryptic promoter is present, then effective transcription from the promoter can be measured by, e.g., transfecting the DNA into eukaryotic cells and measuring the level of transcription resulting therefrom.

The above described DNA, i.e., a DNA which is capable of being transcribed into RNA in a bacterium, wherein the RNA is capable of being translated in a eukaryotic cell or is an antisense RNA or a catalytic RNA, and the one or more DNA molecules encoding one or more polymerases can be present on one plasmid or more than one plasmid. Introduction of one or more plasmids in the bacterium can be performed according to methods well known in the art, e.g., electroporation or chemical transformation techniques.

In a preferred embodiment, the DNA molecules encoding said RNA are integrated into the bacterial chromosome. A bacterial RNA delivery system in which the DNA encoding the RNA is integrated into the bacterial chromosome is referred to herein as "chromosomal-based RNA delivery system". Such a system is described in the Examples. Methods for integrating a DNA sequence into a bacterial chromosome are also set forth in Hone et al. (1988) *Microbial. Pathogenesis* 5:407; Strugnell et al. *Gene* 88:57 (1990); and Hohman et al. (*Proc. Natl. Acad. Sci. U.S.A.* 92:2904 (1995)). In a preferred embodiment, chromosomal integration is achieved by first introducing a hisOG deletion mutation into the target bacterial strain; the hisOG deletion is then replaced by the complete hisOG region and the segment of heterologous DNA of interest. One advantage of a chromosomal-based RNA delivery system is that recombinant plasmids are not delivered to the target eukaryotic cell, thereby decreasing the risk of forming mutations in the nuclear DNA of the target cell.

In yet another embodiment, the RNA is introduced into the bacterium for delivery to the eukaryotic cell. The RNA can be, e.g., synthesized in vitro using, e.g., an in vitro transcription system. Alternatively, the RNA can be isolated from a source, and can be, e.g., a mixture of different RNAs. In one embodiment, the RNA is RNA extracted from a pathogenic organism. In an even more preferred embodiment, a specific population of RNA from a pathogenic organism is selected, preferably a population of RNA which does not encode pathogenic proteins, and introduced in the bacterium. The RNA can be introduced into bacteria using the same methods for introducing DNA into bacteria. For example, RNA can be introduced by electroporation or chemical transformation.

5. Exemplary Uses

The bacterial compositions and methods of the invention are useful for delivering RNA to a eukaryotic cell, wherein the RNA is capable of being translated into a protein or peptide, or is an antisense RNA or a catalytic RNA.

In a preferred embodiment, the invention provides an RNA vaccine. In an even more preferred embodiment, the RNA vaccine is a mucosal vaccine which can be delivered via routes other than parenteral, e.g., oral or nasal route. Such methods of delivery may be more convenient for vaccination than parenteral administration. It is known that the mucosal and systemic immune systems are compartmentalized (Mesteky, *J. Clin. Immunol.*, 7:265–270 (1987); Newby, In: *Local Immune Response of the Gut,* Boca Raton, CRC Press, Newby and Stocks Eds., pages 143–160 (1984); and Pascual et al., *Immuno. Methods.*, 5:56–72 (1994)). Thus, antigens delivered to mucosal surfaces elicit mucosal and systemic responses, whereas parentally delivered antigens elicit mainly systemic responses but only stimulate poor mucosal responses (Mesteky, supra). Another advantage of delivery of antigen to mucosal surfaces is that mucosal stimulation at one mucosal site (for example the intestine) can result in development of immunity at other mucosal surfaces (for example genital/urinary tract) (Mesteky, supra). This phenomenon is referred to as the common mucosal system and is well documented (Mesteky, supra; and Pascual et al, supra).

The development of mucosal vaccines has been hindered by the poor immunogenicity of antigens when delivered by these routes. In this context, antigens can be divided into two classes: those that bind to intestinal surfaces and those that do not bind, where the former are significantly more immunogenic than the latter (De Aizpurua et al, *J. Exp. Med.*, 176:440–451 (1988)). Similarly, delivery of RNA molecules to mucosal surfaces is inefficient due to the many natural host defenses found at these surfaces, such as the gastric barrier and nucleases in the gastrointestinal tract, and the glycocalyx layer in the respiratory tract. Accordingly, the invention provides a method for eliciting mucosal and systemic responses by efficiently delivering RNA encoding an antigen to mucosal surfaces.

The method of the invention can also be carried out in such a way to limit spreading of the virus from the target site. This could be accomplished by any of several methods including delivery of a very limited dose, delivery of a severely attenuated auxotrophic strains, such as an asd mutant (Curtiss et al, supra) that will be rapidly inactivated or die, or delivery of a bacterial strain that contains attenuating lesions. In a preferred embodiment, the bacterium is modified to contain a suicide system (Rennell et al, supra; and Reader et al, supra), i.e., a gene encoding a toxic product, e.g., a toxin, under the control of a strong promoter, such as the anaerobic nirB promoter (Harborne et al, supra) or an inducible promoter. Accordingly, a bacteria containing a suicide gene under the control of a nirB promoter is capable of inducing the death of the bacteria once the bacterium has entered the cytoplasm of a target cell. A bacterium containing a suicide gene is capable of inducing the death of the bacteria upon induction with an appropriate stimulatory agent. In addition, cytochalasin can be used to inhibit entry of all intracellular bacteria into cells. Accordingly, the invention provides methods that allow control of the fate of the bacteria once these are introduced into a subject.

In a preferred embodiment of the invention, the invasive bacteria containing the RNA molecules, and/or DNA encoding such, are introduced into an animal by intravenous, intramuscular, intradermal, intraperitoneally, peroral, intranasal, intraocular, intrarectal, intravaginal, intraosseous, oral, immersion and intraurethral inoculation routes.

The amount of the live invasive bacteria of the present invention to be administered to a subject will vary depending on the species of the subject, as well as the disease or condition that is being treated. Generally, the dosage employed will be about $10^3$ to $10^{11}$ viable organisms, preferably about $10^5$ to $10^9$ viable organisms per subject.

The invasive bacteria of the present invention are generally administered along with a pharmaceutically acceptable carrier and/or diluent. The particular pharmaceutically acceptable carrier an/or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al, *J. Clin. Invest.*, 79:888–902 (1987); and Black et al *J. Infect. Dis.*, 155:1260–1265 (1987)), or bicarbonate buffer (pH 7.0) containing ascorbic acid, lactose, and optionally aspartame (Levine et al, *Lancet*, II:467–470 (1988)). Examples of carriers include proteins, e.g., as found in skim milk, sugars, e.g., sucrose, or polyvinylpyrrolidone. Typically these carriers would be used at a concentration of about 0.1–30% (w/v) but preferably at a range of 1–10% (w/v).

Set forth below are other pharmaceutically acceptable carriers or diluents which may be used for delivery specific routes. Any such carrier or diluent can be used for administration of the bacteria of the invention, so long as the bacteria are still capable of invading a target cell. In vitro or in vivo tests for invasiveness can be performed to determine appropriate diluents and carriers. The compositions of the invention can be formulated for a variety of types of administration, including systemic and topical or localized administration. Lyophilized forms are also included, so long as the bacteria are invasive upon contact with a target cell or upon administration to the subject. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the composition, e.g., bacteria, of the invention can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

For administration by inhalation, the pharmaceutical compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated in rectal, intravaginal or intraurethral compositions such as suppositories or retention enemas, e.g., containing conventional suppository bases such as cocoa butter or other glycerides.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the bacteria of the invention are formulated into ointments, salves, gels, or creams as generally known in the art, so long as the bacteria are still invasive upon contact with a target cell.

The compositions may, if desired, be presented in a pack or dispenser device and/or a kit which may contain one or more unit dosage forms containing the active ingredient. The pack may for example comprise metal or plastic foil, such as a blister pack. The pack or dispenser device may be accompanied by instructions for administration.

The invasive bacteria containing the RNA expression cassette can be used to infect animal cells that are cultured in vitro, such as cells obtained from a subject. These in vitro-infected cells can then be introduced into animals, e.g., the subject from which the cells were obtained initially, intravenously, intramuscularly, intradermally, or intraperitoneally, or by any inoculation route that allows the cells to enter the host tissue. When delivering RNA to individual cells, the dosage of viable organisms to administered will be at a multiplicity of infection ranging from about 0.1 to $10^6$, preferably about $10^2$ to $10^4$ bacteria per cell.

In yet another embodiment of the present invention, bacteria can also deliver RNA molecules encoding proteins to cells, e.g., animal cells, from which the proteins can later be harvested or purified. For example, a protein can be produced in a tissue culture cell.

The present invention is further illustrated by the following examples which should not be construed as limiting in any way. The contents of all cited references including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); Immobilized Cells And Enzymes (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

EXAMPLES

Example 1

RNA Delivery Using a Bacterial Vector

This Example provides evidence that bacteria can be used as a vehicle for delivering RNA into eukaryotic cells, where the RNA is subsequently translated. Accordingly, this Example describes the modification of Shigella to contain (i) a β-galactosidase gene, containing eukaryotic translation elements, under the control of a T7 promoter; and (ii) a gene encoding a T7 polymerase under the control of a bacterial promoter, and that contacting of Hela cells with such modified Shigella bacteria results in efficient expression of β-galactosidase RNA transcribed in the bacteria in the HeLa cells.

A. Modification of Shigella for Use as an RNA Delivery Vehicle

For efficient translation of β-galactosidase RNA in eukaryotic cells, the β-galactosidase gene was cloned downstream of the cap-independent translation enhancer (CITE) sequence from encephalomyocarditis virus (Duke et al, *J. Virol*, 66:1602–1609 (1992)). This sequence allows for efficient translation of an RNA in the absence of a 7 methyl-guanosine at the 5' end of the RNA.

The LacZ gene encoding the bacterial β-galactosidase gene was cloned in the pCITE4 vector (Novagen, Inc., Madison, Wis.). Expression vector pCITE4 contains a T7 promoter sequence juxtaposed and upstream of a CITE sequence which in turn is upstream of several unique cloning sites. Downstream of the cloning sites are sequences encoding a poly-A tail and T7 transcription terminator. Accordingly, the T7 polymerase promoter in pCITE4 allows high-level expression of the mRNA containing the CITE sequence fused to the β-galactosidase gene. pCITE4 vector further comprises a gene providing resistance to ampicillin. This plasmid is referred to herein as pCITE4-LacZ.

To supply T7 polymerase in trans, plasmid pGB-T7 was constructed. This plasmid was derivatived from streptomycin-resistant low copy plasmid pGB2 and expresses the T7 polymerase under the control of the in vivo-inducible anaerobic *E. coli* nirB promoter (see, e.g., Chatfield et al. (1992) *Biotechnology* 10:888). In short, plasmid pGB2 (Churchward, G. et al. (1984) *Gene* 31:165) was digested with restriction endonucleases SalI and PstI (Sambrook et al., supra) and ligated to a PCR generated fragment encoding the nirB promoter resulting in plasmid pBA-23 (Wu, S. et al. (1997) *AIDS Research and Human Retroviruses* 13:1187). Then the sequences encoding T7 RNA polymerase were excised from plasmid pGP1-2 by digesting with SmaI and SalI (Tabor, S. and C. C. Richardson (1992) *Biotechnology* 24:280) and inserted into SmaI digested pBA-23 by blunt digestion (Sambrook et al., supra), resulting in plasmid pGB-T7.

The plasmids pCITE4-β-LacZ and pGB-T7 were introduced into attenuated *Shigella flexneri* strain CVD 1203 by electroporation (Hone et al. (1991) *Vaccine* 9:810). This bacterial strain contains deletions in both aroA and virG loci and is further described in Noriega et al. (1994) *Infection & Immunity* 62:5168. Since pCITE4-LacZ and pGB-T7 contain different antibiotic selection markers and compatible replicons, these plasmids will coexist in a single bacterial clone. Control strains having either pGB-T7 or pCITE4-lacZ alone were also constructed by electroporation.

Expression of β-galactosidase-encoding RNA in the transformed bacteria was confirmed by RNA hybridization using the RNeasy™ total RNA isolation system according to the manufacturer's instructions (Qiagen).

Prior to infection of eukaryotic cells, the transformed bacteria were seeded from 30% (w/v) glycerol stocks, maintained at −70° C., onto solid medium (Tryptic Soy Agar, DIFCO, Madison, Wis.) containing 100 μg/ml of ampicillin and 100 μg/ml of streptomycin, to select for bacteria containing the plasmids, and incubated overnight at 37° C.

B. Eukaryotic Cells

HeLa cells (ATCC No. CCL-2) were grown on plastic tissue culture plates at 37° C. in 5% (v/v) $CO_2$ in RPMI medium supplemented with 10% (v/v) fetal bovine serum, 2.0 mM L-glutamine, 1.0 mM L-pyruvate, 50 U/ml penicillin and 50 μg/ml streptomycin (hereinafter "RPMI/FBS"). 24 to 48 hours prior to RNA delivery, the HeLa cells were trypsinized with 0.25% (w/v) trypsin containing 1.0 mM EDTA, and split by limiting dilution such that they were 70–90% confluent at the time of the experiment.

Prior to RNA delivery, the number of HeLa cells present was ascertained by counting in a hemocytometer (Celis, *Cell Biology: A Laboratory Manual*, Ed. Academic Press, San Diego, Calif. (1994)).

C. Delivery of Bacterial RNA and Expression of the Product of Said RNA in Eukaryotic Cells Semi-confluent HeLa cells in 24 well plates (at $5 \times 10^5$ cells/well; Costar) were washed once with RPMI media lacking fetal bovine serum and penicillin/streptomycin (hereinafter "SFM"), then overlaid with each bacterial suspension in SFM, and incubated at 37° C. in 5% $CO_2$. Suspensions of the bacterial RNA delivery vectors were either harvested from overnight agar plates or from a fresh broth cultures as described above, and were inoculated at an infection ratio of approximately $10^1$ to $10^3$ viable transformed bacteria per HeLa cell.

After 3 hours, the SFM containing the extra-cellular bacteria was removed, the HeLa cells were rinsed once with RPMI/FBS, and then fresh RPMI/FBS containing 100 μg/ml gentamicin was added. Following a further 1 hour incubation at 37° C. in 5% $CO_2$, the gentamicin solution was removed, the HeLa cells were rinsed once with RPMI/FBS, fresh RPMI/FBS was added and the cells were returned to 37° C. in 5% $CO_2$.

Survival of the attenuated *S. flexneri* inside of the HeLa cells was determined by counting viable bacteria present in each of 3 wells at 6 hours, 24 hours, 48 hours, 72 hours and 92 hours, post-bactofection (i.e., post contacting of the HeLa cells with the engineered Shigella bacteria) by standard methods (Celis, *Cell Biology: A Laboratory Manual*, Ed, Academic Press, San Diego Calif. (1994)). Briefly, the post-bactofected HeLa cells were lysed with 1.0% (w/v) deoxycholic acid and viable bacteria enumerated on solid media. The results show that the *S. flexneri* strains were rapidly inactivated inside the HeLa cells. This demonstrates that the delivery strain is attenuated and rapidly inactivated in human cells.

At 6 hours, 24 hours, 48 hours, and 72 hours post-inoculation, the HeLa cells were harvested and the β-galactosidase activity was quantitated using standard colorimetric procedures.

The results of this experiment demonstrate the presence of a significant amount of β-galactosidase activity in cells infected by the Shigella vector containing both pCITE-lacZ and pGB-T7 (greater than 200 μU β-galactosidase activity/mg protein). HeLa cells infected with a vector containing either pCITE-LacZ or pGB-T7 alone did not result in any significant β-galactosidase activity (i.e., less than 50 μU β-galactosidase activity/mg protein). Thus, these results indicate that RNA was successfully produced in Shigella and translated in HeLa cells.

Example 2

In Vitro and In Vivo Expression of GFP from an RNA Expression Cassette

This Example describes the construction of an RNA expression cassette encoding a green fluorescent protein (GFP), its introduction into a bacterial vector, and the delivery of the GFP RNA made in the bacterial vector to eukaryotic cells in vitro and in vivo, where it is translated into GFP protein.

A. Development of an RNA Expression Cassette Encoding GFP

To produce a GFP mRNA expression cassette, a DNA sequences encoding GFP from plasmid pEGFP (Clontech, Palo Alto, Calif.) was inserted into plasmid pCITE4a (Novagen Inc., see, Example 1). To accomplish this step, the pEGFP sequence (Genbank accession number U57608) was used to design GFP-specific PCR primers, so that the GFP-encoding sequences from plasmid pEGFP were amplified by PCR using Taq polymerase from the second nucleotide of the second codon to the termination codon. Then, pCITE4a was digested with MscI and BglII (New England Biolabs) to remove unwanted sequences in the cloning region that encode a thrombin digestion site and a His tag. The BglII site was end-filled using T4 DNA polymerase and the PCR-generated GFP sequences were inserted into the resultant linear vector by blunt ligation, resulting in pCITE4::GFP. This ligation produced an in-frame fusion between the start codon in pCITE4a and the GFP-encoding sequences. This plasmid was transformed initially into DH5α (Life Technologies, Bethesda Md.) and characterized by restriction endonuclease digestion and PCR analysis ((Hone et al. (1988) *Microbial Pathogenesis* 5(6): 407–18; Hone et al. (1991) *Vaccine* 9(11): 810–816.; Hone et al. (1994) *Molecular Microbiology* 13(3): 525–30; Foutset al. (1995) *Vaccine* 13(17): 1697–705; Wu et al. (1997) *AIDS Research & Human Retroviruses* 13(14): 1187–94)). Plasmids containing an insert of the anticipated size were sequenced to verify that no PCR-generated errors were introduced.

B. Construction of a Bacterial RNA Delivery Vector for Delivering RNA Encoding GFP to Eukaryotic Cells A prototype bacterial delivery vector was constructed by introducing plasmids pGP1-2 (from F. W. Studier, Biology Department, Brookhaven National Laboratory, Upton N.Y. (Studier and Moffatt (1986) *J Mol Biol* 189(1): 113–30)) and pCITE4::GFP into attenuated Shigella vector strain CVD 1203 by electroporation (Noriega et al. (1994) *Infect. Immun.* 62(11): 5168–72).

Plasmid pGP1-2 expresses T7 polymerase at 37° C. (Studier and Moffatt (1986) *J Mol Biol* 189(1): 113–30). Control strains, referred to herein as V-C1 and V-C2, received pGP1-2 or pCITE4::GFP alone, respectively (see, Table I). The strain containing the two plasmids is referred to herein as H992 (see, Table 1). Following transformation of Shigella with the plasmids, these were characterized by restriction endonuclease digestion and PCR analysis as above, which verified that the correct configurations were present in each strain. Strains that displayed the appropriate genotype were subsequently used to evaluate the efficacy of the plasmid-based RNA delivery system in vitro and in vivo.

TABLE 1

| STRAIN | PLASMID |
| --- | --- |
| H992 | PGP1-2 and pCITE4::GFP |
| V-C1 | pCITE4::GFP |
| V-C2 | PGP1-2 |

C. In vitro Delivery of a GFP RNA Expression Cassette

To evaluate the delivery of the GFP RNA expression cassette in vitro, 70–80% confluent HeLa cells were treated (multiplicity of infection (moi) of 10) with strains H992, V-C1 and V-C2 as described (Powell et al. (1996) *Introduction of eukaryotic expression cassettes into animal cells using a bacterial vector delivery system.* New York, Cold Spring Harbor Press). Positive control cells were transfected with lipofectamine®-treated pEGFP DNA, according to the instructions provided by the manufacturer (Lifetechnologies). GFP expression was examined at 24, 48 and 72 hr post infection by UV microscopy.

The results indicate that at 24 hr after treatment, strong GFP expression was observed in approximately 10% of the cells transfected with pEGFP (Clontech) and approximately 0.5% of the HeLa cells treated with strain H992. As expected, no discernable GFP expression was observed in wells treated with V-C1 and V-C2. Visible expression of GFP following treatment with H992 was mainly transient, since GFP was essentially not detectable 72 hr after treatment. This observation suggests that the expression of the Shigella-delivered GFP RNA is essentially short lived in this Example, which is consistent with the life-span of RNA molecules as compared to the more stable expression that is observed following transfection with DNA expression cassettes. Therefore, this RNA delivery system provides a means for the transient expression of genes in host cells. However, as further describes herein, if desired, the life-span of RNA molecules can be increased.

D. In vivo Delivery of a GFP RNA Expression Cassette

To evaluate the delivery of the GFP RNA expression cassette in vivo, a $10^6$ cfu dose of strain H992 or V-C1 was injected intraperitoneally into 6–8 week old female BALB/c mice. 24 hr after treatment cells expressing GFP were clearly evident in mononuclear cells harvested from the peritoneum of mice treated with H992. On the other hand, no discernable GFP expression was observed in mice treated with control strain V-C1.

Thus, this Example demonstrates the efficient production of a protein in eukaryotic cells in vitro and in vivo by contacting the cells with a bacterial vector containing an RNA expression cassette encoding the protein.

Example 3

Stimulation of an Immune Response by a Bacterial gp120 RNA Vaccine Vector

This Example describes the construction of a Human Immunodeficiency Virus 1 (HIV-1) gp120 RNA expression cassette, its inclusion in a bacterial vector, and the administration of the bacterial vector into a host organism which results in the development of an immune response against gp120 in the host.

A. Construction of a Human Immunodeficiency Virus 1 gp120 RNA Expression Cassette DNA sequences encoding gp120 of HIV-1 strain MN from plasmid pMN-ST1 (kindly provided by Dr. Marv Reitz, Institute of Human Virology) ((Lori et al. (1992) *J Virol* 66(8): 5067–74)) were inserted into plasmid pCITE4a (Novagen Inc.). To accomplish this step, the gp120-encoding sequences from plasmid pMN-ST1 were amplified by PCR using Taq polymerase according to the procedure of the manufacturer (Stratagene) from the second nucleotide of the second codon to the termination codon. Then, pCITE4a was digested with MscI and BglII (New England Biolabs) as described in Example 2. The BglII site was end-filled using T4 DNA polymerase and the PCR-generated GFP sequences was inserted into the resultant linear vector by blunt ligation, resulting in pT7-CITE::120. This ligation produced an in-frame fusion between the start codon in pCITE4a and the gp120-encoding sequences. This plasmid was transformed initially into DH5α (Life Technologies, Bethesda Md.) and characterized by restriction endonuclease digestion and PCR analysis ((Hone et al. (1988) *Microbial Pathogenesis* 5(6): 407–18; Hone et al. (1991) *Vaccine* 9(11): 810–816; Hone et al. (1994) *Molecular Microbiology* 13(3): 525–30; Foutset al. (1995) *Vaccine* 13(17): 1697–705; Wu et al. (1997) *AIDS Research & Human Retroviruses* 13(14): 1187–94)). Plasmids containing an insert of the anticipated size were sequenced to verify that no PCR-generated errors were introduced. The resultant plasmid was designated pT7-CITE-120.

B. Construction of a Bacterial gp120 RNA Vaccine Vector

Similarly to the procedure described in Example 2 above, a prototype bacterial gp120 RNA vaccine vector was constructed by introducing plasmids pGP1-2 (from F. W. Studier, Biology Department, Brookhaven National Laboratory, Upton N.Y., (Studier and Moffatt (1986) *J Mol Biol* 189(1): 113–30); Expresses T7 polymerase) and pT7-CITE::120 into attenuated Shigella strain CVD 1203 (generously donated by M. Levine, School of Medicine, University of Maryland, Baltimore Md. (Noriega et al. (1994) *Infect. Immun.* 62(11): 5168–72)) by standard electroporation procedures described previously ((Noriega et al. (1994) Infect. Immun. 62(11): 5168–72)). A control strain received pT7-CITE::120 alone. Following transformation the plasmid were characterized by restriction endonuclease digestion and PCR analysis as above, which verified that the correct configurations were present in each strain. Strains that displayed the appropriate genotype were subsequently used to evaluate the efficacy of the plasmid-based RNA vaccine delivery system in vivo.

C. Immunogenicity of a Bacterial gp120 RNA Vaccine Vector

This example describes the characterization of the immunogenicity of Shigella strain CVD 1203 bearing both plasmids, pGP1-2 and pT7-CITE::120 (strain referred to as H1015) in BALB/c mice in which the RNA vaccine vector was inoculated intranasally. Control mice received CVD 1203 containing pT7-CITE::120 only (referred to as H1011). Groups of 5 BALB/c mice were vaccinated intranasally with a single $10^6$ dose of strains H1011 or H1015 as described ((van de Verg et al. (1995) *Infection & Immunity* 63(5): 1947–54)).

To measure gp120-specific immune responses, the mice were sacrificed 28 days after vaccination, and splenocytes (SCs) were prepared as described (Foutset al. (1995) *Vaccine* 13(17): 1697–705). The presence and the amount of V3-specific CD8+ T cells was then determined using an IFN-γ-specific ELISPOT assay (Chada et al. (1993) *Journal of Virology* 67(6): 3409–17). In this assay, 10ME fibroblasts which were pulsed with peptide P18, which is located in the V3 region (Takeshita et al. (1995) *Journal of Immunology* 154(4): 1973–86), were used as stimulators. The results of this assay showed that gp120 RNA vaccine strain H1015 elicited a net 37.5 V3-specific IFN-γ-secreting T cells per $10^6$ splenocyte above the baseline V3-specific IFN-γ-secreting T cell response established by vaccination with the control strain.

Depletion of CD8+ T cells but not of CD4+ T cells from the immune splenocytes resulted in a loss of the V3-specific responsiveness in the splenocytes from the mice vaccinated with H1015, indicating that the response was largely mediated by CD8+ T cells. This result is encouraging in light of the extensive data implicating CD8+ T cells in the control of, and protection against, HIV-1 ((Walker et al. (1988) *Science* 240(4848): 64–6; Walker and Levy (1989) *Immunology* 66(4): 628–30; Walker et al. (1989) *Cell Immunol* 119(2): 470–5; Shen et al. (1991) *Science* 252(5004): 440–3; Walker, C. M. (1993) *Seminars in Immunology* 5(3) :195–201; Walker et al. (1991) *J Virol* 65(11): 5921–7; Abimiku et al. (1995) *AIDS Research & Human Retroviruses* 11(3): 383–93; Cocchi et al. (1995) *Science* 270 (5243): 1811–5; Lohman et al. (1995) *Journal of Immunology* 155(12): 5855–60; Miller et al. (1997) *Journal of Virology* 71(3): 1911–21; Garzino-Demo et al. (1998) *AIDS Res Hum Retroviruses* 14 Suppl 2: S177–84; Price et al. (1998) *Curr Biol* 8(6): 355–8)).

Thus, this Example shows that eukaryotic RNA expression cassettes can be used as vaccines. In particular, an RNA expression cassette encoding HIV gp120 can be used as a vaccine against HIV. This is of particular importance, in view of the fact that several lines of evidence attest to the importance of vaccine-induced immunity against gp120 of human immunodefficiency virus 1 (HIV-1; (Berman et al. (1990) *Nature* 345(6276): 622–5; Emini et al. (1990) *J Viro* 164(8): 3674–8; el-Amad et al. (1995) *Aids* 9(12): 1313–22; Berman et al. (1996) *J Infect Dis* 173(1): 52–9; Boyer et al. (1996) *Journal of Medical Primatology* 25(3): 242–50; Lubeck et al. (1997) *Nature Medicine* 3(6): 651–8)). Similarly, cell-mediated immunity against gp120 has also been associated with the control of HIV-1 replication ((Koup et al. (1989) *Blood* 73(7): 1909–14; Koup et al. (1994) *Journal of Virology* 68(7): 4650–5; Safrit et al. (1994) *Journal of Immunology* 153(8): 3822–30)). Collectively, these references bear strong evidence that immunity against HIV-1 gp120 is capable of affording protection against HIV-1.

Example 4

Delivery of RNA Encoding HIV-1 Env Gene Product

This example describes a system permitting the delivery of RNA encoding the HIV-1 envelope (HIV env) protein to HeLa cells by an engineered Shigella bacteria, and efficient translation of the RNA in HeLa cells. The advantage of expressing HIV-1 env in human cells as opposed to bacterial expression is the ability of human cells to glycosylate and produce an oligomeric Env structure that closely resembles Env expressed in HIV-1 infected individuals (Earl et al. (1994) *J. Virol.* 68:3015).

To produce an Env mRNA expression cassette, DNA sequences encoding HIV-1$_{MN}$ env are cloned from plasmid pMN-ST1 into plasmid pCITE4a (Novagen, Inc., Madison, Wis.) as follows. The HIV-1 Env-encoding sequences from plasmid pMN-ST1 (described in Lori et al. (1992) *J. Virol.* 66:5067) are amplified by PCR using Vent polymerase from the second nucleotide of the second codon to the termination codon. pCITE4a is digested with MscI and BglII (New England Biolabs) to remove unwanted sequences in the cloning region that encode a thrombin digestion site and a His tag. The BglII site is end-filled using T4 DNA polymerase (MscI creates blunt-ends) and the PCR-generated Env sequences are inserted into the resultant linear vector by blunt ligation, resulting in pCITE4-env$_{MN}$. This ligation produces a transcriptional fusion between pCITE4a and the Env encoding sequences.

To construct a vector delivery strain, plasmids pGB-T7 (see Example 1) and pCITE4-env$_{MN}$ are co-transformed into attenuated Shigella vector strain CVD 1203 (Noriega et al., supra) by electroporation as described above.

Following transformation, the plasmids are characterized by restriction endonuclease digestion and PCR analysis as above to verify that the correct configurations are present in each strain. In addition, expression of Env-encoding RNA by each construct is confirmed by RNA hybridization using the RNeasy$^R$ total RNA isolation system according to the manufacturer's instructions (Qiagen). Strains that display the appropriate genotype and RNA profile can be subsequently used to evaluate the efficacy of such a plasmid-based RNA delivery system in vitro and in vivo.

To evaluate the delivery and expression of Shigella-vectored Env RNA vaccines, 70–80% confluent HeLa cells will be treated with a range of doses (multiplicity of infection (moi) from 1 to 1000) of each Shigella vector as described above. The first series of experiments will involve Shigella vectors having plasmids pCITE4-env$_{MN}$ and pGB-T7 alone or in combination. The second series of experiments will involve Shigella vectors having plasmids pnirB-T7 and pCITE4-env$_{MN}$, alone or in combination. As controls, lipofectamine-treated pCITE4-env$_{MN}$ DNA and pRc/CMV:-env will be transfected into HeLa cells or HeLa cells pretreated with vaccinia T7 (vT7) (provided by the AIDS Repository, NIAID), which expresses T7 in the cytoplasm of infected cells, to provide T7 polymerase for the expression of env. Cells treated with the bacterial vectors or the control cells will be harvested following incubation at 37° C. in 5% CO$_2$ for 3, 6, 24, 48 and 72 hrs. The cells will be washed twice with PBS and lysed in 1×SDS sample buffer and run on SDS-PAGE gels made with 5% to 15% gradients of polyacrylamide. The samples will be run under non-reducing and reducing conditions to estimate the yields of oligomeric forms of gp160 (Env).

The cell samples will also be transferred to PVDF membranes which will be probed with a mixture of monoclonal antibodies specific for defined epitopes of gp120 and gp41 (Abacioglu et al. (1994) *AIDS Res. Hum. Retroviruses* 10:371). The extent of glycosylation of Env proteins will be estimated by treatment with Endo-H prior to separation and evidence of glycosylation will be taken as sine qua non that the Env RNA was expressed in the eukaryotic cell. The Env protein will be characterized further for CD4 binding and epitope exposure using capture ELISA methods and published criteria (Abacioglu et al., supra, Moore et al. (1994) *J. Virol.* 68:6836, Poignard et al. (1996) *J. Exp. Med.* 183:473).

Example 5

Chromosomal-Based RNA Delivery and Expression System

This example describes an RNA delivery and expression system using an attenuated Shigella vector CVD 1203 with the T7-driven RNA expression cassettes integrated in the bacterial chromosome. This RNA delivery system presents several advantages, including the absence of delivery of plasmid DNA to the eukaryotic cells, thereby preventing random integration of the plasmid DNA in the eukaryotic chromosomal DNA.

This Example describes integration of these constructs into sequences immediately upstream of hisOGD. In previous studies it was found that this region could accommodate a 7 kb fragment that expressed an *E. coli* fimbrial antigen (Hone et al. (1988) *Microbial Pathogenesis* 5:407). More importantly, the integrated sequences were highly stable both in vitro and in vivo (Hone et al., supra) and did not adversely affect the invasiveness of the bacterial vector. Using this system, integration is achieved in two steps. First, a hisG deletion is introduced into the target strain using plasmid pADE172 (Hone et al., supra). Second, the sequences encoding the integrand are introduced into the mutant allele, resulting in rescue of a his$^+$phenotype (Hone et al., supra). In short, PCR generated fragments spanning P$_{nirB}$-pol$_{T7}$ and P$_{T7}$-CITE-env$_{MN}$, either in combination or alone will be introduced into PstI digested pADE 171 by blunt-end ligation. As before, each construct that displays the appropriate restriction endonuclease digestion pattern and PCR profile will be sequenced to ensure that no errors were introduced as a result of PCR infidelity. The resulting plasmids will then be introduced into CVD 1203, as above. The presence of the integrands will be verified by PCR analysis and DNA hybridization analysis. In addition, expression of Env-encoding RNA by each construct will be confirmed by RNA hybridization as described above. Strains that display the appropriate genotype and RNA profile will be subsequently used to evaluate the efficacy of a chromosome-based RNA expression cassette in vitro and in vivo.

Example 6

Delivery of a Reporter Gene in vivo to Animal Tissue

This Example describes in vivo assays in mice to demonstrate the immunogenicity of a Shigella RNA vaccine delivery system by monitoring humoral and cellular immune responses in both the mucosal and systemic compartments. Pretreatment of mice with streptomycin alters the intestinal flora and creates a favorable environment for Shigella invasion of the mouse gastrointestinal tract (Cooper (1959) *Australian J. Exp. Biol. Med. Sci.* 37:193). Thus, this model offers inexpensive means to evaluate RNA vaccine delivery to these tissues. The effectiveness of this delivery system will then be fully investigated in Rhesus monkeys and volunteers.

BALB/c mice, 6–8 weeks old, will be housed in sterilized microisolator cages and maintained on sterile food and water containing streptomycin (1 mg/ml) (Cooper, supra). Strains bearing pGB-T7 will be streptomycin resistant but the chromosomal constructs will be sensitive to this antibiotic. Therefore, the chromosomal constructs must first be made streptomycin-resistant prior to the murine studies. This will be accomplished by isolating spontaneous streptomycin-resistant derivatives of these constructs, which are selected on solid agar containing 1 mg/ml streptomycin. To vaccinate the animals, each mouse will be given 0.2 ml of 50% saturated bicarbonate solution by orogastric intubation as described in Hone et al. (1987) *J. Infect. Diseases* 156:167.

Two separate experiments will be conducted: (1) To evaluate the induction of humoral responses, groups of 5 BALB/c mice will be immunized by orogastric intubation with a single $10^9$ cfu dose of the Shigella constructs. (2) To evaluate T cell-mediated responses, groups of 35 BALB/c mice will be immunized by orogastric intubation with a single $10^9$ cfu dose of the Shigella constructs. These two experimental groups will be boosted 30, 58, and 86 days after the primary dose. The first group will be immunized with Shigella strains containing either of both of the plasmids pGB-T7 and pCITE4:env$_{MN}$, prepared as described above. The second group will be immunized with Shigella strains having the plasmids pGB-T7 and pCITE4:env$_{MN}$, or with Shigella strains having either or both of plasmids pnirB-PolT7 and pT7-CITE-envMN, prepared as described above. Positive control mice will be immunized intranasally with 10 μg HIV-1$_{MN}$ Env mixed with 5 μg cholera toxin, which induces strong Env-specific immunity.

(i) Characterization of Humoral Responses

Blood will be collected from the tail veins of vaccinated mice 14, 28, 42, 56, 70, 84, 98, and 112 days after the primary immunization. The level of Env-specific IgG and IgA will be measured in sera separated from these blood samples by ELISA using purified fully glycosylated HIV-1$_{MN}$ Env as described, e.g., in Abacioglu et al. (1994) *AIDS Res. & Human Retroviruses* 10:371 or in Moore et al. (1994) *J. Virol.* 68:6836 In each ELISA, Env-specific mAbs will be used as a positive control (Abacioglu et al., supra; Moore et al., supra; and Moore (1990) *AIDS* 4:297). In addition, these sera will be used to follow the development of HIV-1 neutralizing antibodies by the quantitative, linear HIV-1 infectivity assay as described, e.g., in Nara et al. (1990) *J. Virol.* 64:3779, Layne et al. (1991) *Virol.* 189:695, Layne et al. (1991) *J. Virol.* 65:3291, and Wu et al. (1995) *J. Virol.* 69:6054, incorporating HIV-1$_{MN}$ (Gurgo et al. (1988) *Virol.* 164:531) to measure homologous neutralization and HIV-1$_{IIIB}$, HIV-1$_{RF}$ as well as primary HIV-1 isolates (from the AIDS Repository, NIAID) to measure clade-specific and cross-clade neutralization (Nara et al, supra, Layne et al., supra, Wu et al, supra).

(ii) Tissue Harvesting for T Cell Assays and Env-specific Antibody Secreting Cells (ASC) in the Lamina Propria Lamina propria antigen-specific antibody secreting cells are a useful and convenient measure of mucosal immunity, since these cells are T cell-dependent and the level of the response correlates with the development of humoral responses at the mucosal surface after immunization. Groups of 5 mice will be sacrificed 7, 14, 28, 42, 56, and 70 days after primary immunization and mononuclear cells (MNCs) from the spleen, small intestine and mesenteric lymph nodes will be prepared as described (Wu S. et al. (1995) *Infection & Immunity* 63:4933–8; Fouts TR et al. (1995) *Vaccine* 13:1697–705; Okahashi N. et al. (1996) *Infection & Immunity* 64:1516–25; Xu-Amano J. et al. (1993) *J. Exp. Med.* 178:1309–20).

(iii) Enumeration of Env-specific ASC in the Lamina Propria

Lamina propria MNCs will be prepared as described (Wu S. et al. supra; Okahashi N. et al. supra; Xu-Amano J. et al. supra.) Standard IgA- and IgG-specific ELISPOT assays will be used to enumerate Env-specific ASC in the lamina propria MNCs; antigens included in this assay included fully-glycosylated Env (Intracel) or diphtheria toxoid (negative control). The results will be expressed as a function of the total IgA or IgG ASCs.

(iv) Characterization of CD4$^+$ T Cell Responses

To measure T cell proliferation, each MNC preparation will be stimulated with purified fully glycosylated HIV-1$_{MN}$ Env (Intracel Inc.) and proliferation will be quantitated by $^3$H-TdR incorporation, as described, e.g., in (Wu S. et al. supra; Fouts TR et al. supra; Okahashi N. et al. supra; Xu-Amano J. et al. supra). Each proliferative assay will include a mitogen (Con A) control, an ovalbumin control, and a dose-response curve to Env (0.01–10 g/ml). Supernatants will also be collected 72 hr after antigenic stimulation and chemokines MIP-1 and MIP-1, and cytokines IL-4, IL-5, IL-6, IL-10, IL-12 and IFN-γ will be measured by ELISA using commercially available reagents. The amount of cytokines secreted will be relevant, e.g., in light of evidence suggesting that TH1 responses correlate with chemokines production (Schrum S. et al. (1996) *J. Immunol.* 157:3598–3604). Specific T cells will be further characterized by chemokine- and cytokine-specific ELISPOT assays for MIP-1, MIP-1, IL-2, IL-4, IL-5, IL-6, IL-10, and IFN-γ production after enrichment of CD4$^+$ T cells using commercially available monoclonal antibodies (R&D Systems and Pharmingen) (Okahashi N. et al. supra; Xu-Amano J. et al. supra).

In addition, MNCs will be cultured in complete medium (CM) only, CM containing fully glycosylated HIV-1$_{MN}$ Env at 0.1–10 or CM containing Shigella outer membrane antigen (10 μg/ml) as shown above. The culture plates will be incubated then for 24 hr at 37° C. in 5% $CO_2$. After stimulation, CD4$^+$ and CD8$^+$ T cells will be isolated by flow cytometry and no fewer than $5 \times 10^5$ of the purified cells will be placed directly into Trizol$^R$ reagent and cDNA will be synthesized; the resultant samples then will be used in quantitative-competitive (QC) PCR reactions to evaluate the relative levels of chemokine and cytokine cDNA sequences. MIP-1, MIP-1, RANTES, TNF, IL-2, IL-4, IL-5, IL-6, and IFN-γ sequence specific RT-PCR primers are designed based on the known sequences of these molecules, e.g., GenBank. Each QC PCR reaction will be conducted in parallel with the same reactions containing of control plasmid DNA at a range of defined concentrations, which encode truncated MIP-1, MIP-1 and RANTES cDNA sequences and will serve as competitive sequences (R&D Systems and National Biosciences Inc). The PCR fragments will be separated by agarose gel electrophoresis, strained with ethidium bromide and scanned using a BioRad UV densitometer. The results will be expressed as arbitrary mRNA units.

(v) Characterization of CD8$^+$ T Cells

CD8+CTL responses have been shown to correlate with reduced viral burdens in acutely infected individuals (Koup RA et al. (1994) *J. Virol.* 68:4650–5; Borrow P. et al. (1994)

J. Virol. 68:6103–10; Koup RA and Ho DD (1994) Nature 3 70:416). It has also, enhanced production of HIV-suppressive activity by CD8+ T cells and chemokines by T cells from infected (Walker C M et al. (1989) Cellular Immunology 119:470–5; Walker C M et al. (1991) J. Virol. 65:5921–7; Hsueh F W et al. (1994) Cellular Immunology 159:271–9) as well as repeatedly-exposed, uninfected individuals (Paxton Wash., et al. (1996) Nature Medicine 2:412–417) correlated with significantly reduced capacity of these cells to support the growth of HIV-1. Furthermore, protective immunity against a rectal SIV challenge in Rhesus macaques, after direct immunization with SIV Env and p27 into the iliac lymph nodes, correlated with the development of HIV-suppressive, chemokine-secreting CD8+ T cells (Lehner, T. et al. (1996) Nature Medicine 2:767–75) in the draining nodes.

To characterize HIV-specific chemokine-secreting CD8+ T cell responses, a further group of mice will be immunized as above. On days 7, 14, 28, 42, 56, and 70 after immunization, groups of 5 mice will be sacrificed and MNCs from the spleens, the intestinal epithelial layer and lamina propria, and mesenteric lymph nodes will be prepared as described above. The MNCs will be divided into total, CD4+ T cell-depleted and CD8+ T cell-depleted cells, and will be cultured in (i) CM only, (ii) CM containing PHA (Flynn J L et al. (1990) Molecular Microbiology 4:2111–8), (iii) CM containing BC-lacZ fibroblasts expressing galactosidase (Aggarwal A. et al. (1990) J. Exp. Med. 172:1083–90) or (iv) CM containing BC-env fibroblasts expressing gp160 (Abimiku, A G et al. (1995) AIDS Research & Human Retroviruses 11:383–93). The stimulator cells will be titrated in the range of 1000 to 500000 cells per well. The cells then will incubated for 72 hr at 37° C. in 5% $CO_2$ and supernatants will be collected every 24 hr and stored at −80° C. These supernatants will be used to quantitate the levels of MIP-1, MIP-1, TNF-α, IL-2, IL-4, IL-5, IL-6 and IFN-γ by ELISA (see above). In addition, after stimulation CD8+ T cells will be isolated from total MNC cultures by flow cytometry to obtain a minimum of $5 \times 10^5$ cells, which will be placed directly into Trizol$^R$ reagent and cDNA will be synthesized; QC PCR reactions will be used to evaluate the relative levels of chemokine and cytokine cDNA.

(vi) Class I Restricted CTL Responses

After 5 days of such stimulation HIV-specific CTL activity will be measured at both mucosal and systemic effector sites with methodology appropriate to the site (Chada S. et al. (1993) J. Virol. 67:3409–17; Fujihashi K. et al. (1990) J. Immunol. 145:2010–9): the spleen will serve as the systemic site and intestinal intraepithelial and lamina propria lymphocytes will serve as the mucosal sites. CTL activity will be measured using targets $^{51}$Cr-labeled (i) BC-lacZ fibroblast or (ii) BC-env fibroblast (Chada S. et al., supra; Fujihashi K. et al., supra). When killing is observed, the effector cells will be phenotyped using standard methods applied by our group previously (Aggarwal A. et al., supra). For quantitative comparisons, CTL responses will be expressed in lytic units/$10^6$ cells.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A live-invasive bacterium, wherein said bacterium comprises a DNA molecule encoding a therapeutic protein operably linked to a first prokaryotic promoter or bacteriophage promoter such that an RNA molecule encoding said therapeutic protein is transcribed in the bacterium, wherein said RNA molecule comprises a eukaryotic translation element such that said RNA molecule is translated in a eukaryotic host cell, but is not translated in the bacterium, wherein said eukaryotic translation element is a Cap Independent Translation Enhancer (CITE) sequence.

2. The live-invasive bacterium of claim 1, wherein said bacteriophage promoter is the T7 promoter, and wherein said bacterium further comprises a DNA molecule encoding T7 polymerase operably linked to a second prokaryotic promoter so as to allow transcription of said RNA molecule in said bacterium upon expression of said DNA molecule encoding T7 polymerase.

3. The live-invasive bacterium of claim 2, wherein said first or second prokaryotic promoter is the *E. coli* nirB promoter or llp promoter.

4. The live-invasive bacterium of claim 1, wherein said DNA molecule encoding a therapeutic protein is integrated into the bacterium's chromosome.

5. The live-invasive bacterium of claim 2, wherein said DNA molecule encoding T7 polymerase is integrated into the bacterium's chromosome.

6. The live-invasive bacterium of claim 1, wherein said therapeutic protein is a vaccine antigen.

7. The live-invasive bacterium of claim 1, wherein said therapeutic protein is an immunoregulatory agent.

8. The live-invasive bacterium of claim 1, wherein said bacterium is selected from the group consisting of Shigella spp, Listeria spp., Rickettsia spp and enteroinvasive *Escherichia coli*.

9. The live-invasive bacterium of claim 1, wherein said bacterium is selected from the group consisting of Yersinia spp., Escherichia spp., Klebsiella spp., Bordetella spp., Neisseria spp., Aeromonas spp., Franciesella spp., Corynebacterium spp., Citrobacter spp., Chlamydia spp., Hemophilus spp., Brucella spp., Mycobacterium spp., Legionella spp., Rhodococcus spp., Pseudomonas spp., Helicobacter spp., Salmonella spp., Vibrio spp., Bacillus spp., Leishmania spp. and Erysipelothrix spp. which have been genetically engineered to mimic the invasion properties of Shigella spp., Listeria spp., Rickettsia spp., or enteroinvasive *E. coli* spp.

10. The live-invasive bacterium of claim 1, wherein said bacterium has been modified to increase its invasive potential.

11. The live-invasive bacterium of claim 10, wherein said bacterium has been modified with an invasion factor.

12. The live-invasive bacterium of claim 11, wherein said invasion factor is invasin.

13. The live-invasive bacterium of claim 1, wherein said bacterium is attenuated.

14. A composition comprising the bacterium of any of claims 1 or 2–12, and a pharmaceutically acceptable carrier.

15. A eukaryotic host cell comprising the bacterium of any of claims 1 or 2–12, and a pharmaceutically acceptable carrier.

16. The eukaryotic host cell of claim 15, wherein said eukaryotic host cell is a mammmalian cell.

17. The eukaryotic host cell of claim 16, wherein said mammalian cell is selected from the group consisting of a human, bovine, ovine, porcine, feline, canine, goat, equine, donkey, and primate cell.

18. The eukaryotic host cell of claim 17, wherein said mammalian cell is a human cell.

19. A method for introducing and expressing an RNA molecule encoding a therapeutic protein in animal cells comprising infecting said animal cells with live-invasive bacteria, wherein said bacteria comprise a DNA molecule encoding a therapeutic protein operably linked to a first prokaryotic promoter or bacteriophage promoter such that an RNA molecule encoding said therapeutic protein is transcribed from said DNA molecule in the bacteria, wherein said RNA molecule comprises a eukaryotic translation element such that said RNA molecule is translated in said animal cells, but is not translated in the bacteria, wherein said eukaryotic translation element is a Cap Independent Translation Enhancer (CITE) sequence, and wherein said animal cells are cultured in vitro.

20. The method of claim 19, wherein said bacteriophage promoter is the T7 promoter, and wherein said bacteria further comprises a DNA molecule encoding T7 polymerase operably linked to a second prokaryotic promoter so as to allow transcription of said RNA molecule in said bacteria upon expression of said DNA molecule encoding T7 polymerase.

21. The method of claim 19, wherein said prokaryotic promoter is the *E. coli* nirB promoter or llp promoter.

22. The method of claim 19, wherein said DNA molecule encoding a therapeutic protein is integrated into the bacteria's chromosome.

23. The method of claim 20, wherein said DNA molecule encoding T7 polymerase is integrated into the bacteria's chromosome.

24. The method of claim 19, wherein said therapeutic protein is a vaccine antigen.

25. The method of claim 19, wherein said therapeutic protein is an immunoregulatory agent.

26. The method of claim 19, wherein said animal cells are mammalian cells.

27. The method of claim 26, wherein said mammalian cells are selected from the group consisting of human, bovine, ovine, porcine, feline, buffalo, canine, goat, equine, donkey, deer, and primate cells.

28. The method of claim 27, wherein said mammalian cells are human cells.

29. The method of claim 19, wherein said invasive bacteria are selected from the group consisting of Shigella spp, Listeria spp., Rickettsia spp and enteroinvasive *Escherichia coli.*

30. The method of claim 19, wherein said invasive bacteria are selected from the group consisting of Yersinia spp., Escherichia spp., Klebsiella spp., Bordetella spp., Neisseria spp., Aeromonas spp., Franciesella spp., Corynebacterium spp., Citrobacter spp., Chlamydia spp., Hemophilus spp., Brucella spp., Mycobacterium spp., Legionella spp., Rhodococcus spp., Pseudomonas spp., Helicobacter spp., Salmonella spp., Vibrio spp., Bacillus spp., Leishmania spp. and Erysipelothrix spp. which have been genetically engineered to mimic the invasion properties of Shigella spp., Listeria spp., Rickettsia spp., or enteroinvasive *E. coli* spp.

31. The method of claim 19, wherein said bacteria have been modified to increase their invasive potential.

32. The method of claim 31, wherein said bacteria have been modified with an invasion factor.

33. The method of claim 32, wherein said invasion factor is invasin.

34. The method of claim 19, wherein said invasive bacteria are attenuated.

35. The method of claim 19, wherein said animal cells are infected at a multiplicity of infection ranging from about 0.1 to $10^6$.

36. The method of claim 35, wherein said animal cells are infected at a multiplicity of infection ranging from about $10^2$ to $10^4$.

37. A method for immunizing a subject comprising infecting said subject with attenuated live-invasive bacteria, wherein said bacteria comprise a DNA molecule encoding a vaccine antigen operably linked to a first prokaryotic promoter or bacteriophage promoter such that an RNA molecule encoding said vaccine antigen is transcribed in the bacteria, wherein said RNA molecule comprises a eukaryotic translation element such that said RNA molecule is translated in said subject, but is not translated in the bacteria, wherein said eukaryotic translation element is a Cap Independent Translation Enhancer (CITE) sequence, and wherein said vaccine antigen is expressed at levels sufficient to induce an immune response in the subject.

38. The method of claim 37, wherein said bacteriophage promoter is the T7 promoter, and wherein said bacterium further comprises a DNA molecule encoding T7 polymerase operably linked to a second prokaryotic promoter so as to allow transcription of said RNA molecule in said bacterium upon expression of said DNA molecule encoding T7 polymerase.

39. The method of claim 38, wherein said first or second prokaryotic promoter is the *E. coli* nirB promoter or llp promoter.

40. The method of claim 37, wherein said DNA molecule encoding a vaccine antigen is integrated into the bacterium's chromosome.

41. The method of claim 38, wherein said DNA molecule encoding T7 polymerase is integrated into the bacterium's chromosome.

42. The method of claim 37, wherein said bacterium is selected from the group consisting of Shigella spp, Listeria spp., Rickettsia app and enteroinvasive *Escherichia coli.*

43. The method of claim 37, wherein said bacterium is selected from the group consisting of Yersinia spp., Eacherichia spp., Klebsiella spp., Bordetella spp., Neisseria spp., Aeromonas spp., Franciesella spp., Corynebacterium spp., Citrobacter spp., Chlamydia spp., Hemophilus spp., Brucella spp., Mycobacterium spp., Legionella spp., Rhodococcus spp., Pseudomonas spp., Helicobacter app., Salmonella app., Vibrio spp., Bacillus spp., Leishmania app. and Erysipelothrix spp. which have been genetically engineered to mimic the invasion properties of Shigella spp., Listeria spp., Rickettsia spp., or enteroinvasive *E. coli* spp.

44. The method of claim 37, wherein said bacterium has been modified to increase its invasive potential.

45. The method of claim 44, wherein said bacterium has been modified with an invasion factor.

46. The method of claim 45, wherein said invasion factor is invasin.

47. The method of claim 37, wherein said subject is infected with about $10^3$ to $10^{11}$ of said attenuated live-invasive bacteria.

48. The method of claim 47, wherein said subject is infected with about $10^5$ to $10^9$ of said attenuated live-invasive bacteria.

49. The method of claim 37, wherein said attenuated live-invasive bacteria are administered by a route selected from the group consisting of intravenous, intramuscular, intradermal, intraperitoneal, peroral, intranasal, intraocular, intrarectal, intravaginal, intraosseous, oral immersion and intraurethral.

50. The method of claim 37, wherein said attenuated live-invasive bacteria are administered to a mucosal surface of said subject.

* * * * *

SEQUENCE LISTING

<160> NUMBER OF SEQ ID NOS: 2

<210> SEQ ID NO 1
<211> LENGTH: 499
<212> TYPE: DNA
<213> ORGANISM: Encephalomyocarditis virus

<400> SEQUENCE: 1

```
gttattttcc accatattgc cgtcttttgg caatgtgagg gcccggaaac ctggccctgt    60
cttcttgacg agcattccta ggggtctttc ccctctcgcc aaaggaatgc aaggtctgtt   120
gaatgtcgtg aaggaagcag ttcctctgga agcttcttga agacaaacaa cgtctgtagc   180
gaccctttgc aggcagcgga accccccacc tggcgacagg tgcctctgcg gccaaaagcc   240
acgtgtataa gatacacctg caaaggcggc acaacccag tgccacgttg tgagttggat    300
agttgtggaa agagtcaaat ggctctcctc aagcgtattc aacaagggc tgaaggatgc    360 ccagaaggta ccccattgta tgggatctga tctgggcct cggtgcacat gctttacatg    420
tgtttagtcg aggttaaaaa acgtctaggc cccccgaacc acggggacgt ggttttcctt    480
tgaaaaacac gatgataat                                                499
```

<210> SEQ ID NO 2
<211> LENGTH: 4

-continued

```
<212> TYPE: DNA
<213> ORGANISM: Prokaryotic Ribosome Binding Site

<400> SEQUENCE: 2 agga                                                                      4
```